United States Patent [19]
Kato et al.

[11] Patent Number: 5,993,658
[45] Date of Patent: Nov. 30, 1999

[54] METHOD FOR BIODEGRADING TRICHLOROETHYLENE AND METHOD FOR BIODEGRADING CHLORINATED ORGANIC COMPOUND BY MICROORGANISMS

[75] Inventors: Kinya Kato, Yokohama; Shinya Kozaki, Kawasaki; Takeshi Imamura, Atsugi; Toshiyuki Komatsu, Hiratsuka, all of Japan

[73] Assignee: Canon Kabushiki Kaisha, Tokyo, Japan

[21] Appl. No.: 08/707,497

[22] Filed: Sep. 24, 1996

Related U.S. Application Data

[63] Continuation of application No. 08/608,966, Feb. 29, 1996, abandoned, which is a continuation of application No. 08/138,031, Oct. 19, 1993, abandoned.

[30] Foreign Application Priority Data

| Feb. 18, 1993 | [JP] | Japan | 5-029316 |
| Feb. 18, 1993 | [JP] | Japan | 5-029317 |
| Oct. 18, 1993 | [JP] | Japan | 5-259741 |

[51] Int. Cl.$^6$ ........................................... C02F 3/34
[52] U.S. Cl. .................. 210/611; 210/908; 210/909; 435/262.5; 435/874
[58] Field of Search ........................... 210/601, 610, 210/611, 908, 909; 435/262, 874–877, 262.5

[56] References Cited

U.S. PATENT DOCUMENTS

| 4,877,736 | 10/1989 | Fiermans | 435/183 |
| 4,925,802 | 5/1990 | Nelson et al. | 435/262 |
| 5,024,949 | 6/1991 | Hegeman et al. | 435/262 |

FOREIGN PATENT DOCUMENTS

| 567102 | 10/1993 | European Pat. Off. . |
| 2-92274 | 4/1990 | Japan . |
| 3-292970 | 12/1991 | Japan . |
| WO92/19738 | 11/1992 | WIPO . |

OTHER PUBLICATIONS

Gibson et al., "Oxidative Degradation . . . ", Biochem., vol. 7, No. 7, Jul. 1968, pp. 2653–2662.
Whittenbury et al., "Enrichment, Isolation . . . ", J. Gen. Microbiol., vol. 6I, Part 2, May 1970, pp. 205–218.
Dakin et al., "Lactobacilli Causing Spoilage . . . ", J. Appl. Bact., vol. 34, No. 3, pp. 541–545, Sep. 1971.
Beam et al., "Microbial Degradation . . . ", J. Gen. Microbiol., vol. 82, Part 1, pp. 163–169, May 1974.
Nelson et al., "Aerobic Metabolism . . . ", Appl. & Envir. Microbio., vol. 52, No. 2, pp. 383–384, Aug. 1986.
Wackett et al., "Degradation of Trichloroethylene . . . ", Appl. & Envir. Microbiol., vol. 54, No. 7, pp. 1703–1708, Jul. 1988.
Hashimoto et al., "Identification of Three Kinds . . . ", J. Japan Sewage Soc., vol. 24, No. 273, pp. 27–33 1987 and English Trans. of Article.
Vandenbergh et al., "Metabolism of Volatile . . . ", Appl. & Environ. Microbiol., vol. 54, No. 10, pp. 2578–2579, Oct. 1988.
Arciero et al., "Degradation of Trichloroethylene . . . ", Biochem. & Biophys. Res. Comm., vol. 159, No. 2, pp. 640–643, Mar. 1989.
Embley et al., "Lactobacillus Vaginalis . . . ", Int. Journ. System. Bacter., vol. 39, No. 3, pp. 368–370, Jul. 1989.

(List continued on next page.)

*Primary Examiner*—Thomas G. Wyse
*Attorney, Agent, or Firm*—Fitzpatrick, Cella, Harper & Scinto

[57] ABSTRACT

There are here provided a method for biodegrading trichloroethylene which comprises the step of bringing an aqueous medium containing trichloroethylene into contact with microorganisms having a trichloroethylene degrading ability derived from intestines of termites to degrade trichloroethylene; a method for obtaining the microorganisms; a method for remediating a soil by the use of the microorganisms; and a method for biodegrading an chlorinated organic compound with the microorganisms.

7 Claims, 16 Drawing Sheets

OTHER PUBLICATIONS

Wackett et al., "Survey of Microbial Oxygenases . . . ", Appl. & Environ. Microbiol., vol. 55, No. 11, pp. 2960–2964, Nov. 1989.

Harker et al., "Trichloroethylene Degradation . . . ", Appl. & Environ. Microbiol., vol. 56, No. 4, pp. 1179–1181, Apr. 1990.

Folsom et al., "Phenol & Trichloroethylene . . . ", Appl. & Environ. Microbiol., vol. 56, No. 5, pp. 1279–1285, May 1990.

Ewers et al., "Selection of Trichloroethene . . . ", Arch. Microbiol., vol. 154, No. 4, pp. 410–413, 1990.

Henry et al., "Influence of Endogenous . . . ", Appl. & Environ. Microbiol., vol. 57, No. 1, pp. 236–244, Jan. 1991.

Folsom, et al, "Performance Characterization . . . ", Appl. & Env. Microb., vol. 57, No. 6, Jun. 1991, pp. 1602–1608.

Shields, et al., "Mutants of Ps cepacia . . . ", Appl & Env. Microb., vol. 57, No. 7, Jun. 1991, pp. 1935–1941.

Chem. Abstr., vol. 115, No. 24, Dec. 16, 1991, p. 407, n. 262471t.

Shields et al., "Selecting . . . ", Appl. & Env. Microb., vol. 58, No. 12, Dec. 1992, pp. 3977–3983.

METHOD FOR BIODEGRADING TRICHLOROETHYLENE AND METHOD FOR BIODEGRADING CHLORINATED ORGANIC COMPOUND BY MICROORGANISMS

This application is a continuation of application Ser. No. 08/608,966 filed Feb. 29, 1996, now abandoned, which in turn, is a continuation of application Ser. No. 08/138,031 filed Oct. 19, 1993, now abandoned.

BACKGROUND OF THE INVENTION

1. Field of the Invention

The present invention relates to a method for biodegrading a chloroethylene compound by the use of microorganisms derived from intestines of termites. More specifically, it relates to a biodegradation method useful for the purification of sewage or waste water containing trichloroethylene (TCE), a method for remediating a soil by the utilization of the microorganisms, and a method for obtaining the microorganisms useful for the biodegradation of TCE.

Furthermore, the present invention relates to a biodegradation method using microorganisms in which an chlorinated organic compound degrading activity can be induced with an inducer.

2. Related Background Art

In recent years, various environmental inspections have reported that harmful and less degradable aromatic chemical substances have been detected, and in consequence, much attention has now been paid to environmental pollution with these substances. The influence of these substances on ecological systems is feared.

Therefore, in order to prevent pollution with these less degradable chemical substances, it is required to rapidly develop a technique by which these substances are inhibited from getting into the environment. For example, it is strongly desired to establish a technique by which the less degradable harmful substances can be effectively removed from sewage or waste water. Furthermore, the pollution of a soil with the less degradable harmful substances not only hinders the reutilization of the soil but also causes further escalation of the pollution due to the running of the pollutant into groundwater, which is a serious social problem. Therefore, it is strongly desired to establish a technique by which the escalation of the pollution with the less degradable chemical substances can be prevented and the polluted environment can be remediated.

In particular, TCE is an chlorinated organic compound which has been used in IC industries, dry cleaning and the like, and it is a carcinogen. Thus, the environmental pollution with TCE inclusive of the problem of the soil pollution caused by the pollution of groundwater is a serious social problem. Accordingly, the removal and the degradation of TCE contained in the environment, the purification of sewage or waste water containing TCE, and the remediation of the polluted soil are important themes from the viewpoint of environmental protection.

As a removal treatment and a degradation treatment of TCE, there are an adsorption treatment using active carbon, a degradation treatment utilizing light or heat, and the like. However, a biodegradation treatment using microorganisms is attracting attention from the standpoints of cost and operability.

There is a technique by which the function of microorganisms in a soil is utilized to degrade pollutants in the soil and to thereby eliminate the environmental pollution, and this technique is called bioremediation, because of remediating the soil by the use of the microorganisms. Hence, it can be expected that the bioremediation technique is applied to the remediation of polluted soils such as the vacant lot of a semiconductor manufacturing factory, a site of a metal processing factory, the vacant lot of a chemical plant, and the like.

However, there are not many reports that microorganisms having a TCE degrading ability have been isolated. Examples of the microorganisms having TCE degrading ability are limited, and they include Welchia alkenophila sero 5 (U.S. Pat. No. 4,877,736, ATCC53570), Welchia alkenophila sero 33 (U.S. Pat. No. 4,877,736, ATCC53571), Methylosinus trichosprium OB3b [Whitenbury R. J., Gen. Microbiol, Vol. 61, pp. 205–218 (1970)], Acinetobacter sp. G4 [Nelson M J K et al., Appl. Eviron. Microbiol., Aug., pp. 383–384 (1986); Folsom B. R. et al., Appl. Eviron. Microbiol., May, pp. 1279–1285 (1990); and U.S. Pat. No. 4,925,802, ATCC53617; this bacterium has first belonged to Pseudomonas cepacia but then changed to Acinetobacter sp.], Methylomonas sp. MM2 [Henry S M et al., Appl. Environ. Microbiol., Jan., pp. 236–244 (1991)], Alcaligenes denitrificans ssp. Xylosoxidsans JE75 [Ewers J. et al., Arch. Microbiol., Vol. 154, pp. 410–413 (1990)], Alcaligenes eutrophus JMP 134 [Harker A R & Kim Y. Appl. Environ. Microbiol., Apr., pp. 1179–1181 (1990)], Pseudomonas putida F1 [Gibson D T et al., Biochem., Vol. 7, pp. 2653–2662 (1968); Wackett L. P. & Gibson D. T., Appl. Environ. Microbiol, July, pp. 1703–1708 (1988)], Mycobacterium vaccse JOB5 [Beam H. W. & Perry J. J., J. Gen. Microbiol., Vol. 82, pp. 163–169 (1974); Wackett L. P. et al., Appl. Environ. Microbiol., Nov., pp. 2960–2964 (1989), ATCC29678], Nitrosomonas europaea [Arciero D. et al., Biochem. Biophys. Res. Comm., Vol. 159, pp. 640–643 (1989)], Pseudomonas fluoescens PFL12 [Vandenbergh P. A. & Kunka B. S., Appl. Environ. Microbiol., Oct., pp. 2578–2579 (1988)], Lactobacillus fuctivorans RE [Kunkee, Int. J. Syst. Bact., Vol. 30, pp. 313–314 (1980), J. Appl. Bact., Vol. 34, pp. 541–545 (1971)], Lactobacillus vaginalis sp. nov. [Embley T. M. et al., Int. J. Syst. Bacteriol., Vol. 39, pp. 368–370 (1989), ATCC49540], and Methylosinus trichosprium (Japanese Patent Application Nos. 2-92274 and 3-292970).

In addition, none of the presently known bacteria can meet the practical requirements for the TCE degradation method using the microorganisms and do not possess sufficient degrading ability.

Particularly in the case the microorganisms are used in the soil, it must be considered that the treatment is carried out in a specific environment, i.e. in the soil. The microorganisms to be used are required to have a sufficient TCE degrading activity and to effectively show this activity in the soil, but in the conventionally known bacteria, these points are not sufficient.

Nowadays, the acquisition of the bacteria which can meet practically necessary characteristics is strongly desired.

Such microorganisms are those which preferably have sufficient TCE degrading ability, are different from known bacteria in growth conditions and the like, can be applied to a wide range, are rich in utilizable morphology, and particularly can be effectively utilized in the specific environment of the soil. Examples of such additional requirements include drug resistance and an ability to utilize sucrose.

For example, in the case that the waste water containing TCE is treated, it is required that the microorganisms to be used have a TCE degrading ability, are scarcely damaged in the waste water, and can grow in the severe environment of the waste water. That is, the microorganisms having resistance to many antibiotics and assimilability to various saccharoses can probably successfully grow even in the severe environment.

Thus, the bacteria having the TCE degrading ability and more practically advantageous characteristics than the conventionally known bacteria are strongly required.

Furthermore, in biodegrading chlorinated organic compounds such as TCE, tetrachloroethylene (PCE) and dichloroethylene (DCE) in an environment of a polluted site such as a polluted soil, i.e., an open system, the density of the administered microorganisms by which the biodegradation can be carried out is noticeably decreased owing to predation by protozoans and under the influence of other native bacteria. For this reason, it is often very difficult to increase the density of the microorganisms in compliance with a required treatment ability. In order to increase the density of the microorganisms, there are a method which comprises feeding air to the soil, and a method which comprises forwarding a nutritious solution under pressure. However, although requiring a great deal of energy, these methods cannot effectively increase the number of the bacteria per unit area, and so the treatment ability of these methods remains at a low level on the whole.

In the treatment in a reactor or the like, i.e., in the treatment in a closed system, a good deal of energy for nutrient feed and aeration is also required so as to maintain the density of the microorganisms, as in the above-mentioned open system.

The microorganisms which can degrade the chlorinated organic compounds express an enzyme capable of degrading these compounds, but in order to express this kind of enzyme, an inducer is necessary.

In this case, when a large amount of the inducer is used, the degradation activity of the microorganisms increases, and this fact is known only in an example of tryptophan (WO 90/06901). However, detailed reports regarding the amount of the inducer to be used have not been present at all.

SUMMARY OF THE INVENTION

An object of the present invention is to provide a method for degrading TCE by the utilization of microorganisms.

Another object of the present invention is to provide a method for remediating a soil by the utilization of microorganisms.

Still another object of the present invention is to provide a method for obtaining microorganisms useful for the degradation of TCE.

A further object of the present invention is to provide a method for biodegrading chlorinated organic compounds by heightening degradation activity per unit weight of microorganisms capable of degrading the chlorinated organic compounds, whereby a sufficient degrading treatment ability can be obtained even in an open system such as a soil in which an increase in the number of bacteria cannot be expected.

A still further object of the present invention is to provide a method for biodegrading chlorinated organic compounds by which a satisfactory degradation treatment ability can be obtained even in a closed system and even by a small number of bacteria to permit decreasing energy and cost required for the increase and the maintenance of the bacteria number.

These objects can be accomplished by the following present invention.

That is, the first aspect of the present invention is directed to a method for biodegrading trichloroethylene which comprises the step of bringing an aqueous medium containing trichloroethylene into contact with microorganisms having a trichloroethylene degrading ability derived from intestines of termites to degrade trichloroethylene.

The second aspect of the present invention is directed to a method for obtaining microorganisms having a trichloroethylene degrading ability which comprises the steps of culturing microorganisms separated from the bodies of termites in a culture medium.

The third aspect of the present invention is directed to a method for remediating a soil which comprises the step of bringing trichloroethylene in the soil into contact with microorganisms having a trichloroethylene degrading ability derived from intestines of termites to degrade trichloroethylene.

The fourth aspect of the present invention is directed to a biodegradation method for degrading an chlorinated organic compound by bringing microorganisms, whose degrading activity can be induced with an inducer, into contact with the chlorinated organic compound in the presence of the inducer to degrade the chlorinated organic compound, the amount of the inducer being such as to meet the following relation $$2\int_0^T f(t)dt - T \cdot f(T) \geq 0$$

(wherein T is a culture time when the bacterial number y is maximum),
when the microorganisms are cultured by a batch system in the presence of the inducer and the growth curve of the microorganisms is close to y=f(t) (wherein y is a bacteria number determined by an optical density (O.D.), and t is a culture time).

DESCRIPTION OF THE PREFERRED EMBODIMENTS

Figure 1:
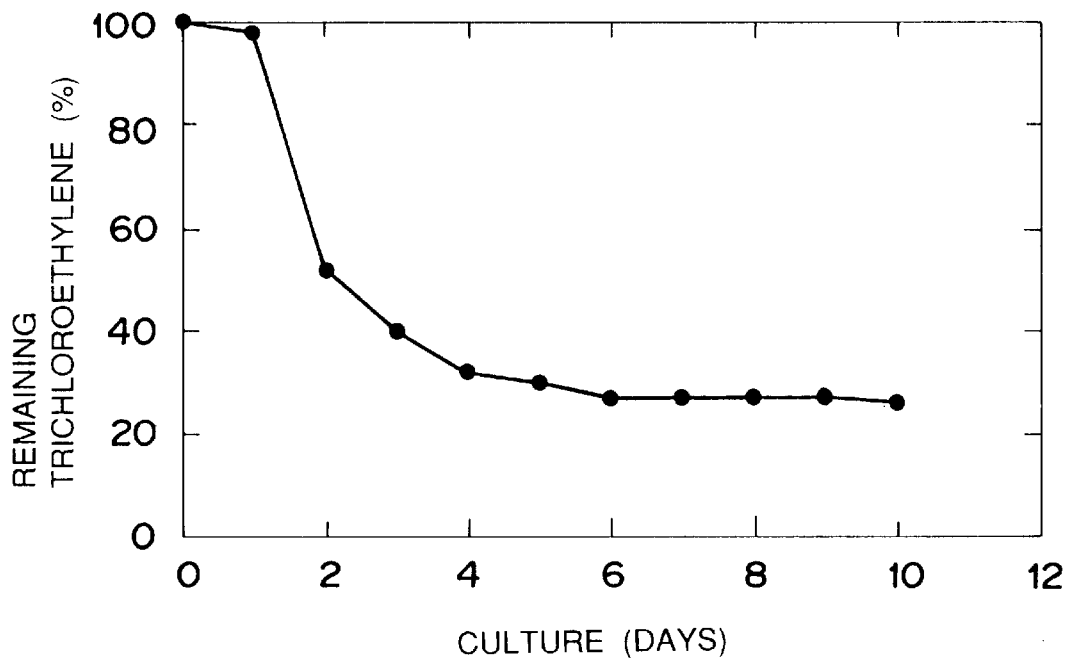
FIG. 1 shows the change by day of a ratio of remaining TCE in Example 1.

The present invention can be roughly classified into two concept.

The first concept is concerned with a method for degrading TCE by the use of microorganisms derived from intestines of termites, a method for remediating a soil, and a method for obtaining the microorganisms.

The second concept is concerned with a method for biodegrading TCE and chlorinated organic compounds by heightening the degrading activity of the microorganisms capable of degrading the chlorinated *Nasutitermes ephratae, Nasutitermes exitiosus, Nasutitermes nigriceps* in a Nasutiterminae genus. Above all, *Nasutitermes takasagoensis* is particularly preferable.

As a culture medium for screening the microorganisms having the TCE degrading ability, there can be utilized a culture medium containing TCE, and if necessary, a carbon source, a nitrogen source, an inorganic salt and a growing factor. For example, in the case of Pseudomonas bacteria, yeast extract and peptone can be used singly or in combination as the nitrogen source, and potassium primary hydrogenphosphate, ammonium chloride or the like can be utilized as the inorganic salt. The concentration of TCE can be suitably selected. Cultivation can be carried out under conditions in compliance with the kind of microorganisms to be separated. In the case that the microorganisms which cannot be grown only by TCE are separated, an isolated strain is cultured in a culture medium containing the carbon source, for example phenol and the like, necessary to grow, and the microorganisms having the TCE degrading ability can be then selected.

The thus separated microorganisms can be used to carry out the degradation treatment of TCE. In the degradation treatment, one kind or a mixed system of two or more kinds of microorganisms having the TCE organic compounds.

In the first place, the first concept of the present invention will be described in detail.

A method for biodegrading TCE of the present invention is characterized by comprising the step of bringing an aqueous medium containing trichloroethylene into contact with microorganisms derived from intestines of termites which have an ability to degrade trichloroethylene, thereby degrading trichloroethylene.

Furthermore, a method for remediating a soil is characterized by comprising the step of bringing, in the soil, trichloroethylene into contact with microorganisms derived from intestines of termites which have an ability to degrade trichloroethylene, thereby degrading trichloroethylene to remediate the soil.

The microorganisms derived from the intestines of termites which can be used in the method of the present invention can be obtained by, for example, sterilizably washing the surfaces of the termites, taking intestines out of the termites and crushing them in a suitable solution, and isolating a strain from a part of the mixture containing the crushed intestines, this strain being screened on the basis of the TCE degrading ability. In the present invention, the various kinds of termites can be used, but preferable examples of the termites include *Nasutitermes takasagoensis*, degrading ability can be used. In the case where the mixed system is used, the microorganisms whose composition is known or unknown but which have the TCE degrading ability can be utilized. Therefore, even when a plurality of kinds of microorganisms are contained in the culture medium for the above-mentioned screening, these microorganisms can be utilized as the mixed system without separation. As the isolated strain, a *Ps. cepacia* strain KK01 or the like can be utilized. Additionally, in the present invention, there can also be used a variant obtained by naturally or artificially varying the microorganisms having the TCE degrading ability separated from intestines of the termites.

The strain KK01 is characterized by growing in the presence of a phenolic compound alone, degrading the phenolic compound, having resistance to antibiotics, utilizing various kinds of saccharoses as shown in the undermentioned examples, and having the TCE degrading ability.

In the present invention, the degradation treatment of TCE can be carried out by bringing TCE in a material to be treated such as waste water into contact with the above-mentioned microorganisms derived from the intestines of the termites. This contact of the microorganisms with the material to be treated is achieved by culturing the microorganisms in the aqueous liquid containing TCE to be degraded, or adding the aqueous liquid to the culture medium of the microorganisms. In this case, an optional process such as a batch process, a semi-continuous process or a continuous process can be used. The microorganisms, when used, may not be fixed or may be fixed on a suitable carrier. The material to be treated such as waste water may be subjected to a suitable pretreatment, if necessary. For example, the adjustment of a TCE concentration or a pH, or the supplementation of various nutrients may be carried out. In the degradation range, the TCE concentration is preferably adjusted to about 100 ppm or less in the presence of another nutrient such as yeast extract.

The method for remediating a soil of the present invention can be carried out by bringing the microorganisms having the TCE degrading ability into contact with TCE in the soil. The contact of the microorganisms with the soil can be achieved by directly introducing the microorganisms into the soil, supporting the microorganisms on a carrier and then introducing the carrier into the soil, or the like. The amount of the microorganisms to be fed to the soil depends upon growing factors of the microorganisms in the soil such as a pollution degree of the soil, a nutritious state, temperature and oxygen concentration.

Next, the second concept of the present invention will be described in detail.

The present inventors have paid attention to and investigated the amount of an inducer to be added at the time of the degradation with the intention of heightening the degradation activity of the microorganisms capable of degrading the chlorinated organic compounds. As a result, they have found that there is correlation between the amount of the inducer which can heighten the degradation activity and the shape of a bacteria growth curve at an early stage of the batch culture of the microorganisms in the presence of the inducer, i.e., the growth characteristics of the microorganisms. That is, it has been found that in order to heighten the degradation activity, the amount of the inducer must be in the range in which the above-mentioned growth curve meets the following relation $$2\int_0^T f(t)dt - T \cdot f(T) \geq 0$$

(wherein T is a culture time when the bacterial number y is maximum), when the microorganisms are cultured by a batch system in the presence of the inducer and the growth curve of the microorganisms is close to y=f(t) (wherein y is a bacteria number determined by an optical density (O.D.), and t is a culture time).

In consequence, the present invention has now been achieved.

The reason why the above-mentioned relation is established cannot be definitely elucidated at present, but this relation has been confirmed with regard to many kinds of microorganisms under many conditions. Furthermore, it has been confirmed that the above-mentioned relation can be applied to a closed batch reactor, an open continuous reactor and a complex heterogeneous system such as a soil.

No particular restriction is put on the microorganisms which can be used in the method of the present invention, so long as they can induce the degradation activity to the chlorinated organic compounds with the aid of the inducer and also have the degradation activity to the inducer. As such microorganisms, there can be utilized unidentified microorganisms, mixed microorganisms which are not isolated, symbiotic microorganisms, and isolated and identified microorganisms. Examples of the identified microorganisms include bacteria belonging to a Pseudomomas genus, an Acinetobactor genus, a Methylocystis genus and a Methylosinus genus, and among them, the bacteria having the above-mentioned characteristics can be used in the present invention. Examples of the usable microorganisms include *Methylosinus trichosporium* OB3b capable of degrading TCE in the presence of methane, and a *Pseudomonas cepacia* strain KK01 which requires phenol as the inducer.

The chlorinated organic compounds to be degraded include ethylene chlorides such as TCE and DCE.

The inducer can be selected in compliance with the kind of microorganisms to be used, and examples of the inducer include methane, and aromatic compounds such as phenol, toluene and cresol.

The method of the present invention can be applied to either of a closed system and an open system such as a waste water treatment and a soil treatment. In addition, the microorganisms may be supposed on a carrier, or an optional technique for accelerating the growth may be employed.

Now, the present invention will be described in more detail in reference to examples, but the scope of the present invention should not be limited to these examples.

In this connection, an M9 culture medium which will be used in the respective examples has the following composition.

Composition of the M9 culture medium (per liter):

| | |
|---|---|
| Na$_2$HPO$_4$ | 6.2 g |
| KH$_2$PO$_4$ | 3.0 g |
| NaCl | 0.5 g |

-continued

| | |
|---|---|
| NH$_4$Cl (pH 7.0) | 1.0 g |

EXAMPLE 1

(The degradation of TCE by microorganisms derived from intestines of termites, and a method for obtaining the microorganisms having a TCE degrading ability from the termites)

10 workers termites of *Nasutitermes takasagoensis* were put in a culture dish, and ethyl alcohol (95%) was then poured thereinto to sterilize the surfaces of the termites. Next, the termites were washed twice with an M9 culture medium containing 0.6 ppm of TCE to remove ethyl alcohol from the surfaces. After the washing, intestines were taken out of the termites, and then crushed in the M9 culture medium containing 0.6 ppm of TCE to obtain a liquid mixture containing the crushed intestines. Next, a part of this mixture was inoculated into an M9 culture medium containing 3 ppm of TCE, 10 ppm of phenol and 0.5% of yeast extract, and then cultured at 30° C. under aerobic conditions. At the time of the passage of predetermined culture days, the culture medium was sampled and then filtered, and the amount of TCE in the resultant filtrate was measured in a usual manner and ratios of remaining TCE corresponding to the culture days were calculated. The obtained results are shown in FIG. 1. In this case, the amount of TCE at the beginning of the cultivation was regarded as 100%. The results indicate that the microorganisms having the TCE degrading ability can be obtained from the intestines of the termites.

EXAMPLE 2

(Acquisition of isolated bacterium strain having TCE degrading ability, and degradation of TCE)

A culture medium (including grown bacteria) obtained by culturing an M9 culture medium (further including 3 ppm of TCE, 10 ppm of phenol and 0.05% of yeast extract) of Example 1 was applied onto the surface of a TCE-containing M9 agar culture medium (including 3 ppm of TCE, 50 ppm of phenol and 1.2% of agar), and then cultured at 30° C. for 2 days. Some colonies were formed on the agar culture medium, and each of these colonies was inoculated into an M9 culture medium (5 ml) containing 0.6 ppm of TCE, 10 ppm of phenol and 0.05% of yeast extract and then cultured at 30° C. for 2 days.

Next, necessary numbers of serum bottles were prepared in which 30 ml of an M9 culture medium containing 3 ppm of TCE, 10 ppm of phenol and 0.05% of yeast extract was placed, and each culture medium (0.1 ml) of the bacteria collected from each of the above-mentioned colonies was inoculated into each of the above-mentioned serum bottles. Afterward, the serum bottles were completely sealed with butyl rubber septums and aluminum seals, followed by cultivation at 30° C. At the time of the passage of predetermined culture days, the amount of TCE in each serum bottle was quantitatively analyzed by a headspace method using gas chromatography, and the microorganisms in the serum bottle in which TCE had been degraded were regarded as the isolated strain of TCE degrading bacteria.

For one of the isolated strains, bacteriological characteristics were inspected, and consequently, the following results were obtained. It has been confirmed that this isolated strain was the same as a strain KK01 (International Deposition No. FERM BP-4235) which was deposited as a novel strain having the ability to degrade phenolic compounds such as phenol, o-cresol, m-cresol and p-cresol in Fermentation Research Institute, Agency of Industrial Science and Technology, Ministry of International Trade and Industry on Mar. 11, 1992 and then changed to the international deposition in accordance with a Budapest treaty on Mar. 9, 1993.

A. Morphological Properties
  (1) Gram stain: Negative
  (2) Size and shape of the bacteria: Bacillus having a length of 1.0–2.0 μm and a width of about 0.5 μm.
  (3) Mobility: Present B. Growth state of the bacteria in each culture medium

| Culture Medium | Culture Temp. (° C.) | Growth State |
| --- | --- | --- |
| Blood agar culture medium | 37 | + |
| Lactose agar culture medium | 37 | + |
| Chocolate agar culture medium | 37 | ++ |
| GMA | 37 | − |
| Scyllo | 37 | − |
| Usual agar culture medium | 4 | − |
| Usual agar culture medium | 25 | ± |
| Usual agar culture medium | 37 | − |
| Usual agar culture medium | 41 | ± |

C. Physiological properties
  (1) Aerobic or anaerobic: Strictly aerobic
  (2) Degradation type of saccharose: Oxidation type
  (3) Production of oxidase: +
  (4) Reduction of silver nitrate: +
  (5) Production of hydrogen sulfide: −
  (6) Production of indole: −
  (7) Production of urease: −
  (8) Liquefaction of gelatin: −
  (9) Hydrolysis of arginine: −
  (10) Decarboxylation of lysine: +
  (11) Decarboxylation of ornithine: −
  (12) Utilization of citric acid: +
  (13) Methylcarbinolacetyl reaction (VP reaction): −
  (14) Detection of tryptophane deaminase: −
  (15) ONPG: −
  (16) Utilization of carbohydrates:
    Glucose: +
    Fruit sugar: +
    Maltose: +
    Galactose: +
    Xylose: +
    Mannitol: +
    White sugar: −
    Lactose: +
    Aesculin: −
    Inositol: −
    Sorbitol: −
    Rhamnose: −
    Melibiose: −
    Amygdalin: −
    L-(+)-arabinose: +

Next, this strain KK01 was inoculated into an M9 culture medium (5 ml) containing 0.6 ppm of TCE, 10 ppm of phenol and 0.05% of yeast extract, and then cultured at 30° C. for 2 days.

Afterward, 30 ml of an M9 culture medium containing 3 ppm of TCE, 10 ppm of phenol and 0.05% of yeast extract was placed in a serum bottle, and 0.1 ml of the above-mentioned strain KK01 culture medium was inoculated into the M9 culture medium in the serum bottle. Afterward, the serum bottle was crimp-sealed with a butyl rubber septum and an aluminum seal, followed by cultivation at 30° C.

Figure 2:
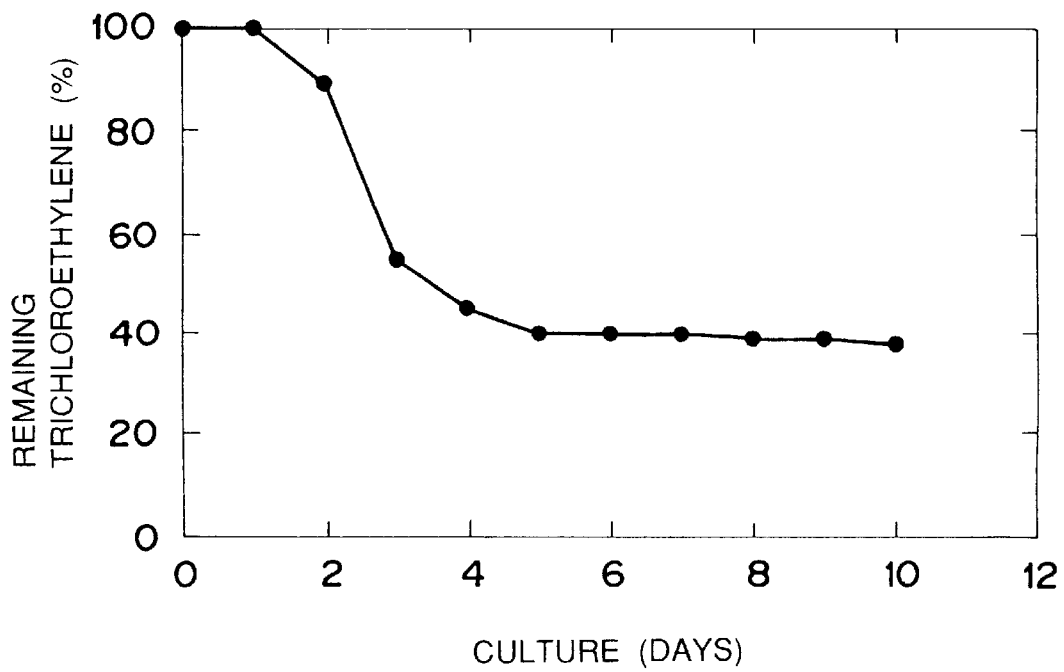
FIG. 2 shows the change by day of a ratio of remaining TCE in a serum bottle in Example 2.

At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 2. In this case, the amount of TCE at the beginning of the cultivation was regarded as a residual ratio of 100%.

EXAMPLE 3

(remediation of a soil by bacteria derived from intestines of termites)

Figure 3:
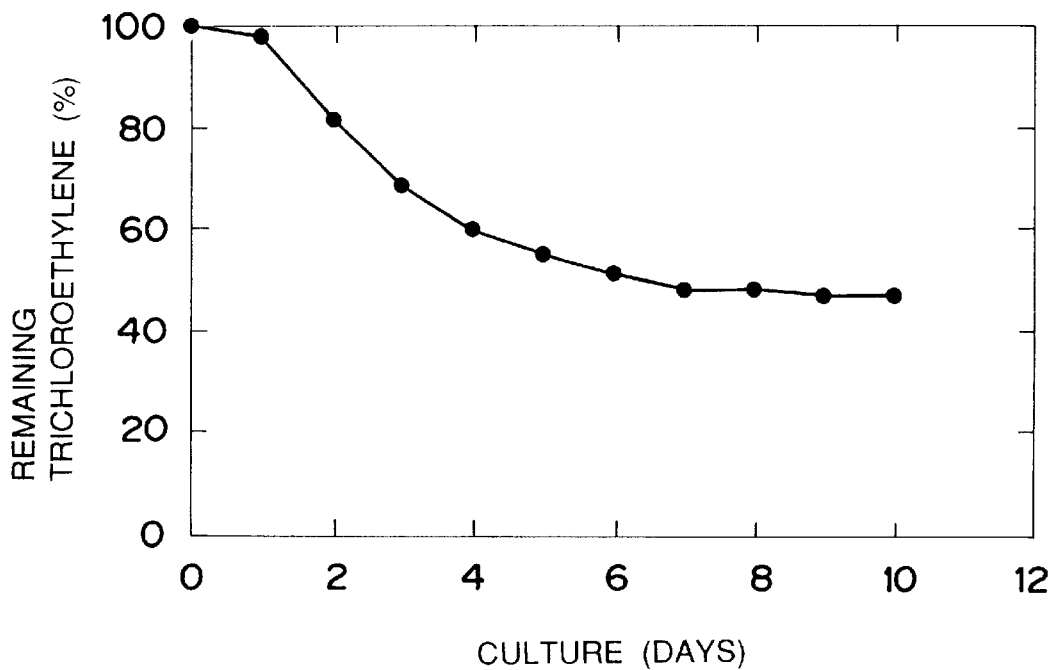
FIG. 3 shows the change by day of a ratio of remaining TCE in a serum bottle in Example 3.

10 workers termites of Nasutitermes takasagoensis were put in a laboratory dish, and ethyl alcohol (95%) was then poured thereinto to sterilize the surfaces of the termites. Next, the termites were washed twice with an M9 culture medium containing 0.6 ppm of trichloroethylene (TCE) to remove ethyl alcohol from the surfaces. After the washing, intestines were taken out of the termites, and then crushed in the M9 culture medium containing 0.6 ppm of TCE to obtain a liquid mixture containing the crushed intestines. Next, 30 ml of a culture medium (an M9 culture medium containing 3 ppm of TCE, 10 ppm of phenol and 0.5% of yeast extract) was placed in a serum bottle, and a sterilized soil was then added thereto till a water surface. Afterward, a part of the liquid mixture containing the crushed intestines was inoculated into the soil, and the serum bottle was then completely sealed with a butyl rubber septum and an aluminum seal, followed by cultivation at 30° C. At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 3. In this case, the amount of TCE at the beginning of the cultivation was regarded as a residual ratio of 100%.

EXAMPLE 4

A strain KK01 was inoculated into an M9 culture medium (5 ml) containing 0.6 ppm of TCE, 10 ppm of phenol and 0.05% of yeast extract, and then cultured at 30° C. for 2 days.

Next, 30 ml of an M9 culture medium containing 3 ppm of TCE, 10 ppm of phenol and 0.5% of yeast extract was placed in a serum bottle, and a sterilized soil was then added thereto till a water surface. Afterward, 0.1 ml of the above-mentioned strain KK01 culture medium was inoculated into the M9 culture medium, and the serum bottle was then crimp-seald with a butyl rubber septum and an aluminum seal, followed by cultivation at 30° C.

Figure 4:
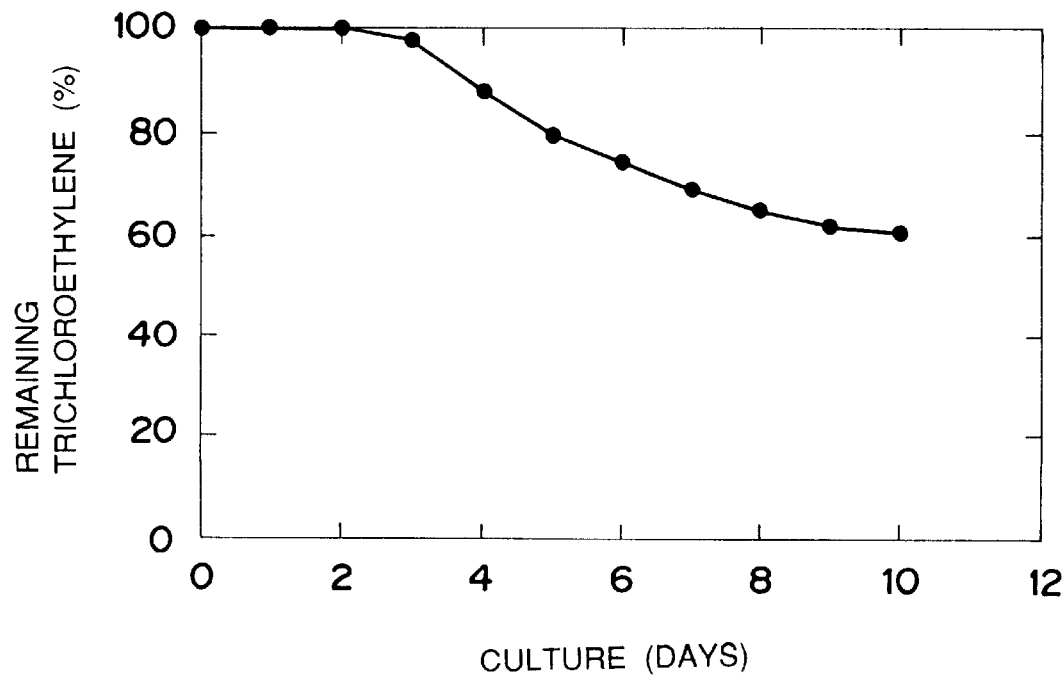
FIG. 4 shows the change by day of a ratio of remaining TCE in a serum bottle in Example 4.

At the time of the passage of predetermined culture days, the amount of TCE in the serum bottle was quantitatively analyzed by a headspace method using gas chromatography, and ratios of remaining TCE corresponding to the culture days were determined. The obtained results are shown in FIG. 4. In this case, the amount of TCE at the beginning of the cultivation was regarded as a residual ratio of 100%.

EXAMPLE 5

A strain KK01 was inoculated into 5 ml of a culture medium (an M9 culture medium containing 1 ppm of TCE, 0.05% of yeast extract and phenol having a predetermined concentration), and then cultured at 30° C. for 2 days.

Next, 15 ml of a culture medium (an M9 culture medium containing 1 ppm of TCE, 0.2% sodium glutamate and phenol having a predetermined concentration) was placed in a serum bottle, and 0.1 ml (inclusive of bacteria) of the above-mentioned strain KK01 culture medium was inoculated into the culture medium in the serum bottle. Afterward, the serum bottle was then completely sealed with a butyl rubber septum and an aluminum seal, followed by cultivation at 30° C. Next, 0.1 ml of the gaseous phase in the serum bottle was sampled with time, and then analyzed by gas chromatography (Gas Chromatogram GC-9AM; made by Shimadzu Seisakusho Ltd.).

Furthermore, the culture medium was sampled, and an absorbance (660 nm) of the culture medium was then measured by a spectrophotometer to determine the number of the bacteria.

Figure 5:
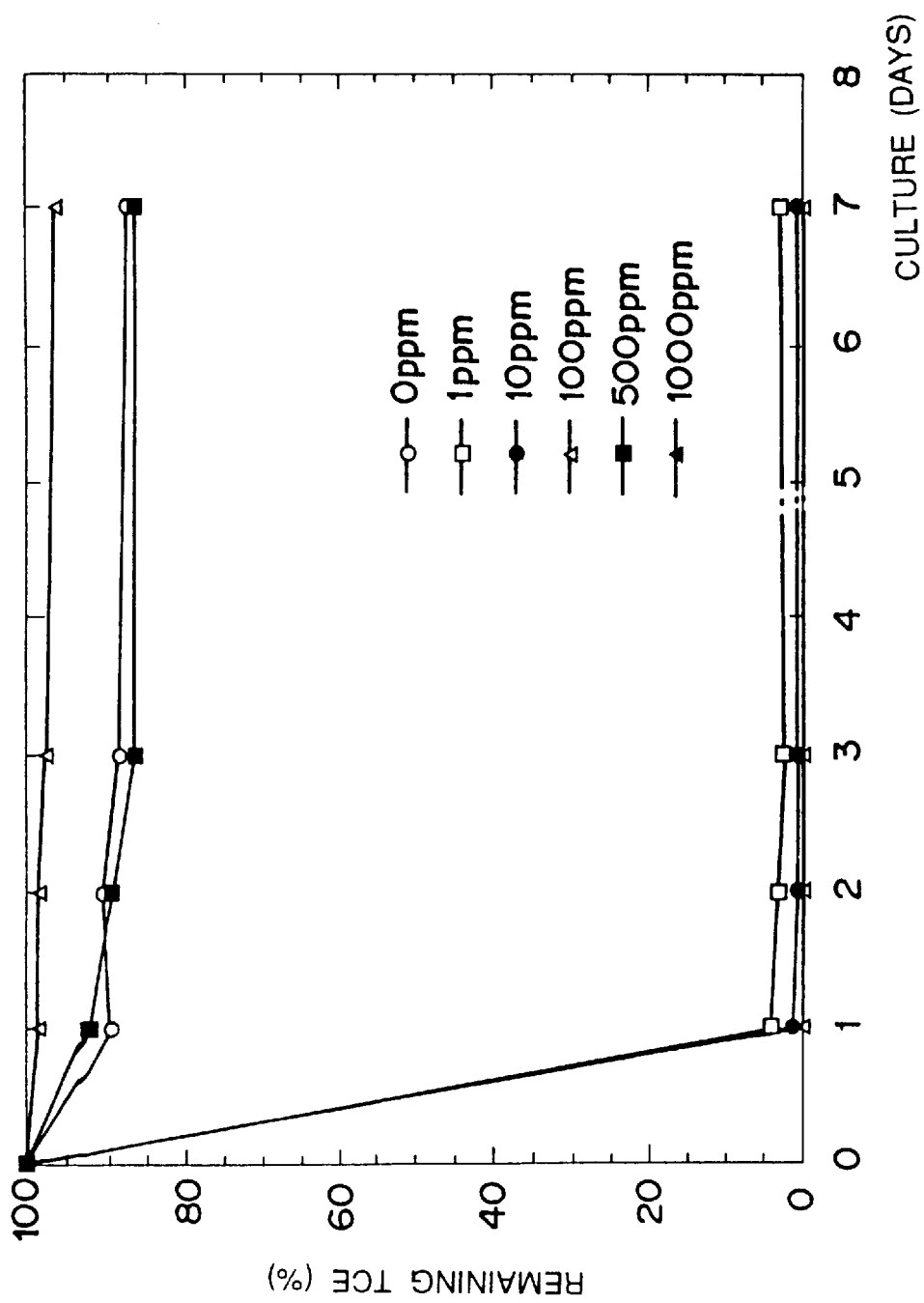
FIG. 5 shows the influence of phenol concentration on TCE degradation in Example 5.
Figure 6:
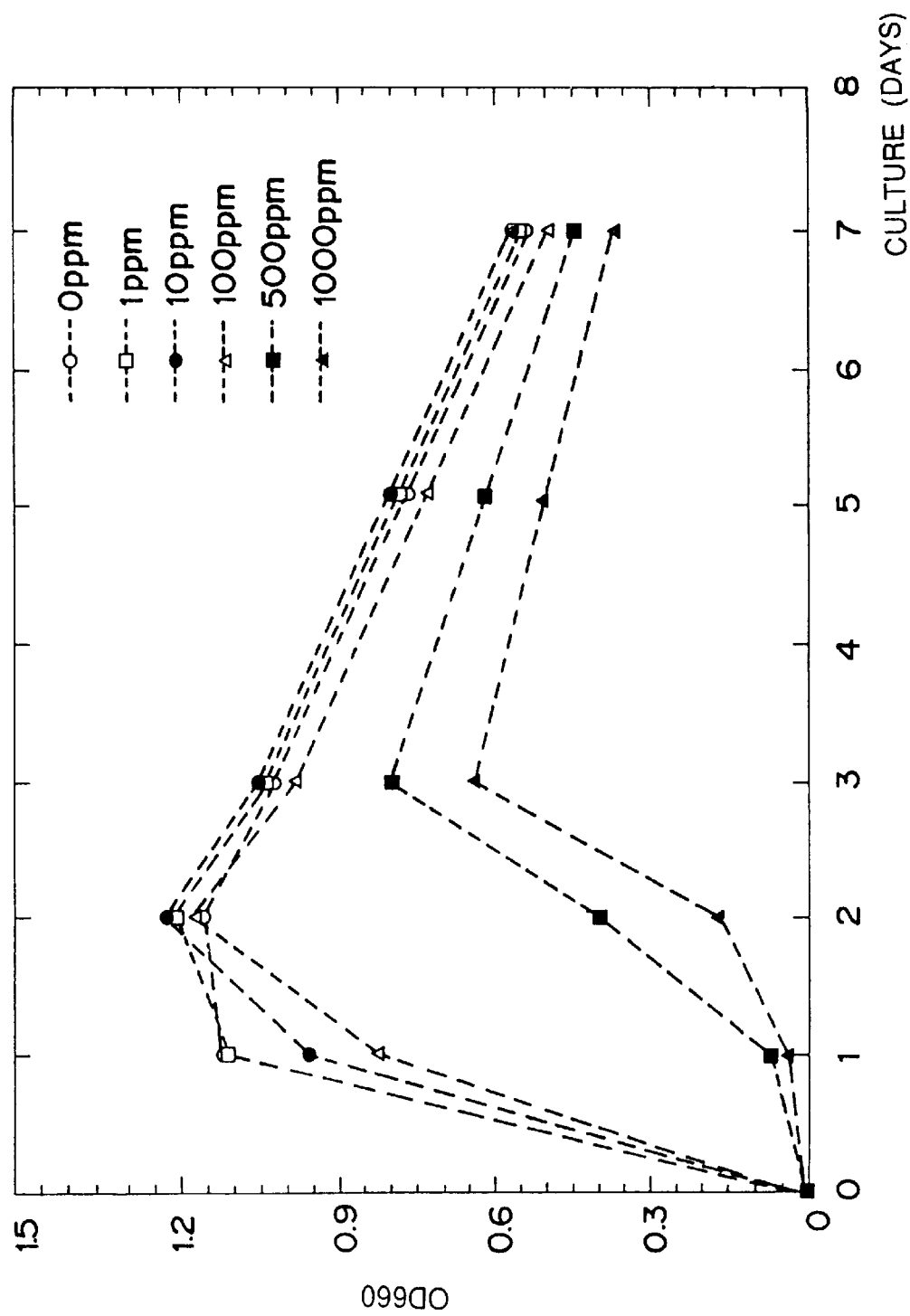
FIG. 6 shows the influence of phenol concentration on the growth of a strain KK01 in Example 5.

In the case that the concentration of phenol which was the inducer was set to 0, 1, 10, 100, 500 and 1,000 ppm, the change of ratios of remaining TCE (which were determined by regarding the amount of TCE at the beginning of the cultivation as 100%) was shown in FIG. 5, and the change of optical density (O.D.) indicating a bacteria number is shown in FIG. 6.

Here, phenol which can be used as the inducer accelerates assimilability as a nutrition for the bacteria to be activated and the expression of a TCE degrading enzyme accompanied thereby, but on the other hand, phenol also inhibits the growth of the bacteria, when its amount is too large.

Therefore, it is necessary to determine the maximum amount of phenol in the range in which the bacteria are not damaged and the degradation activity of the bacteria is increased as much as possible.

FIG. 6 indicates that in the case of a phenol concentration of zero (no phenol is added), the bacteria number increases to O.D.=1.13 in the vicinity of a substantially maximum value (O.D.=1.17 on the second day) on the first culture day, and after the third day, O.D. decreases gradually. This shows the ideal bacteria growth without the hindrance to bacteria growth by phenol. At this time, however, the TCE-degrading enzyme is not expressed, so that the TCE degradation does not occur (FIG. 5).

When the phenol concentration is 1 ppm, O.D. on the first day is 1.12 and O.D. on the second day is a maximum value, i.e., 1.21, and therefore the growth characteristics of the bacteria are scarcely different from the case where the phenol concentration is zero. However, it is apparent that the TCE degradation is drastically improved (FIG. 5). When the phenol concentration is increased up to 10 ppm and 100 ppm, O.D. on the first day is 0.96 (O.D. on the second day is a maximum value, 1.23) and 0.83 (O.D. on the second day is a maximum value, 1.18), respectively, and the growth of the bacteria is gradually hindered on the first day. However, the culture days giving the maximum bacteria number and its maximum value scarcely change within the phenol concentration range of 0 to 100 ppm, and with regard to the decrease of O.D. after the maximum value, the very similar results are shown.

In addition, it is also apparent from FIG. 5 that TCE is also degraded successively.

Particularly in the case of 100 ppm, the degradation proceeded substantially 100%, i.e., up to a detection limit or less of a detector [FID detector (flame ionization detector)] in one day.

On the other hand, when the phenol concentration was 500 ppm and 1,000 ppm, the degradation of TCE did not occur so much. At this time, the growth of the bacteria was noticeably hindered, judging from the fact that O.D. values on the first day at the above-mentioned phenol concentrations were 0.07 and 0.03, respectively. According to the investigation of correlation between various culture growth curves and the ability to degrade TCE and the like, when a culture curve at an early stage till the days giving the maximum O.D. value with respect to the days of the culture shows a substantially convex form, the activity of the bacteria can be heightened. That is, when the microorganisms were cultured by a batch system in the presence of the inducer and the growth curve of the microorganisms is close to y=f(t) (wherein y is a bacteria number determined with an optical density (O.D.), and t is a culture time), and if the concentration of the inducer is set to a value in a range which meets the formula $$2\int_0^T f(t)dt - T \cdot f(T) \geq 0$$

(wherein T is a culture time when the bacterial number y is maximum), the activity of the bacteria can be heightened. More preferably, if the concentration of the inducer is set to the maximum value in this range, the activity of the bacteria per unit amount of the bacteria can be maximized.

If even a small amount of the inducer is contained, it can be presumed that the degradation activity of the bacteria can be enhanced and the biodegradation proceeds. However, from a practical viewpoint, a ratio of the concentration of the inducer to that of the chlorinated organic compound to be degraded is preferably 0.2 or more, more preferably 0.5 or more. Moreover, when the concentration of the chlorinated organic compound is as high as 5 ppm or more, the inducer is used in a ratio of 1 or more so as to obtain good effects.

EXAMPLE 6

Figure 7:
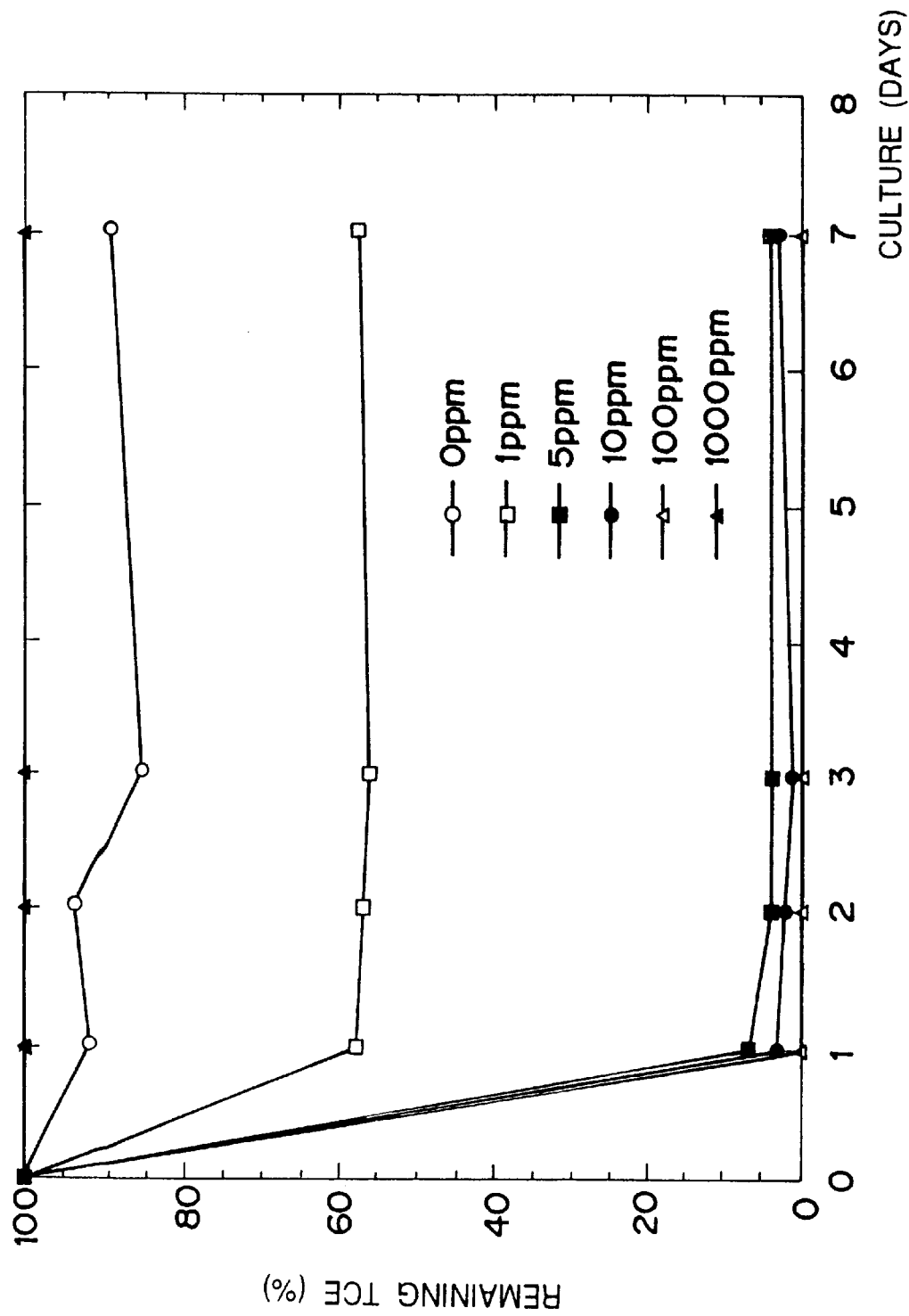
FIG. 7 shows the influence of phenol concentration on TCE degradation in Example 6.
Figure 8:
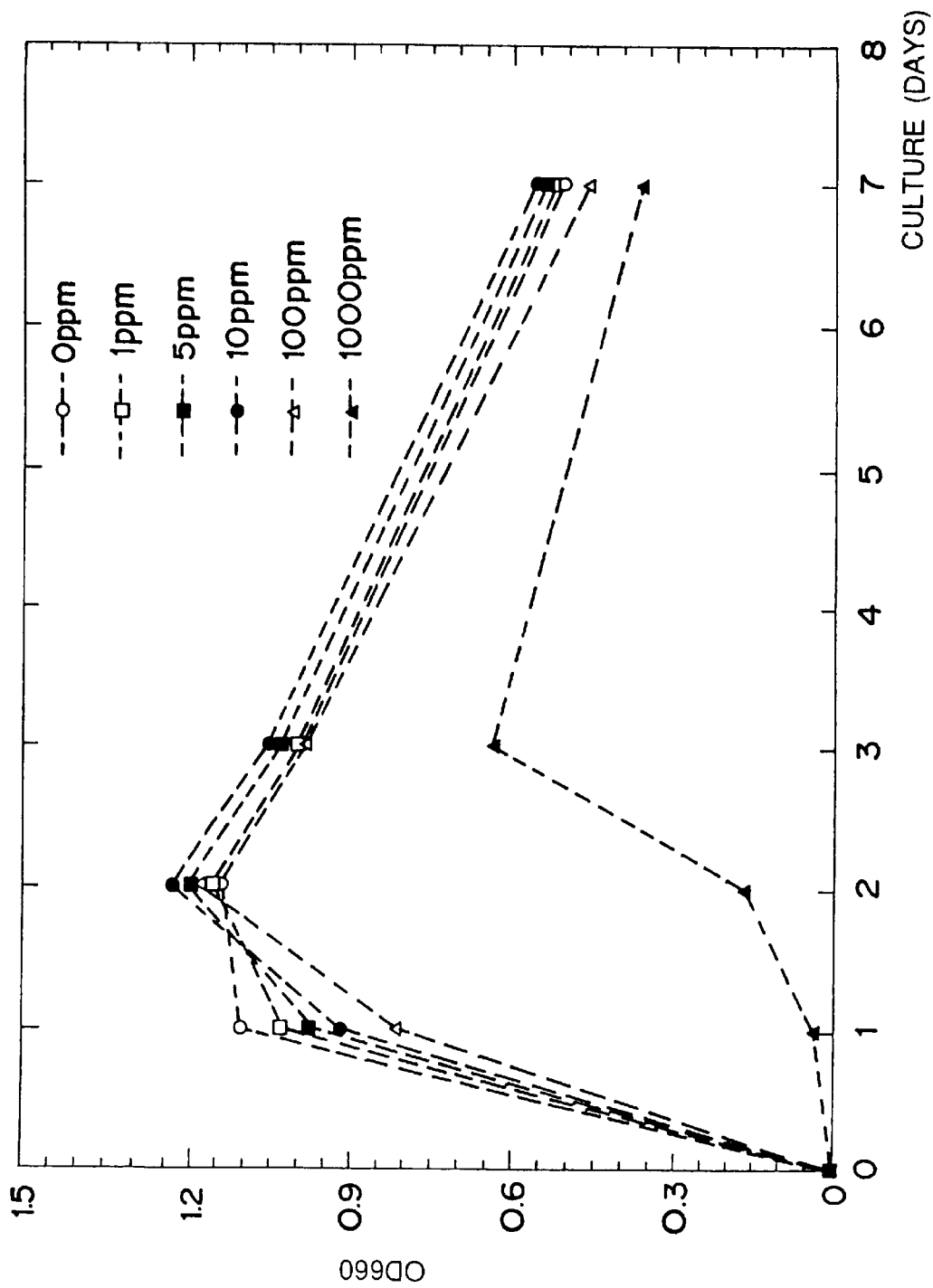
FIG. 8 shows the influence of phenol concentration on the growth of a strain KK01 in Example 6.

An experiment was carried out by the same procedure as in Example 5 except that the concentration of TCE which was a substance to be degraded was set to 5 ppm. The change of ratios of remaining TCE is shown in FIG. 7, and the change of O.D. indicating a bacteria number is shown in FIG. 8.

When the concentration of phenol was 100 ppm, the degradation of TCE proceeded up to a detection limit or less of an FID detector in one day. Even when the concentration of phenol was 1, 5 and 10 ppm, degradations of about 62, 93 and 97% were observed in one day, respectively. On the contrary, when no phenol was added and when the phenol concentration was 1,000 ppm, the degradation of TCE was scarcely observed.

On the other hand, with regard to the growth of the bacteria, when the phenol concentration was 100 ppm or less, all of initial growth curves showed a convex form, and a maximum bacteria number (O.D.=about 1.2) was reached in two culture days. When the phenol concentration was 1,000 ppm, the bacteria growth was apparently hindered, and a period of one day or more were more taken to reach the maximum bacteria number than when the phenol concentration was 100 ppm.

EXAMPLE 7

Cultivation was carried out by the same procedure as in Example 5 except that the concentration of TCE was set to 30 ppm. The obtained results are set forth in FIGS. 9 and 10.

Figure 9:
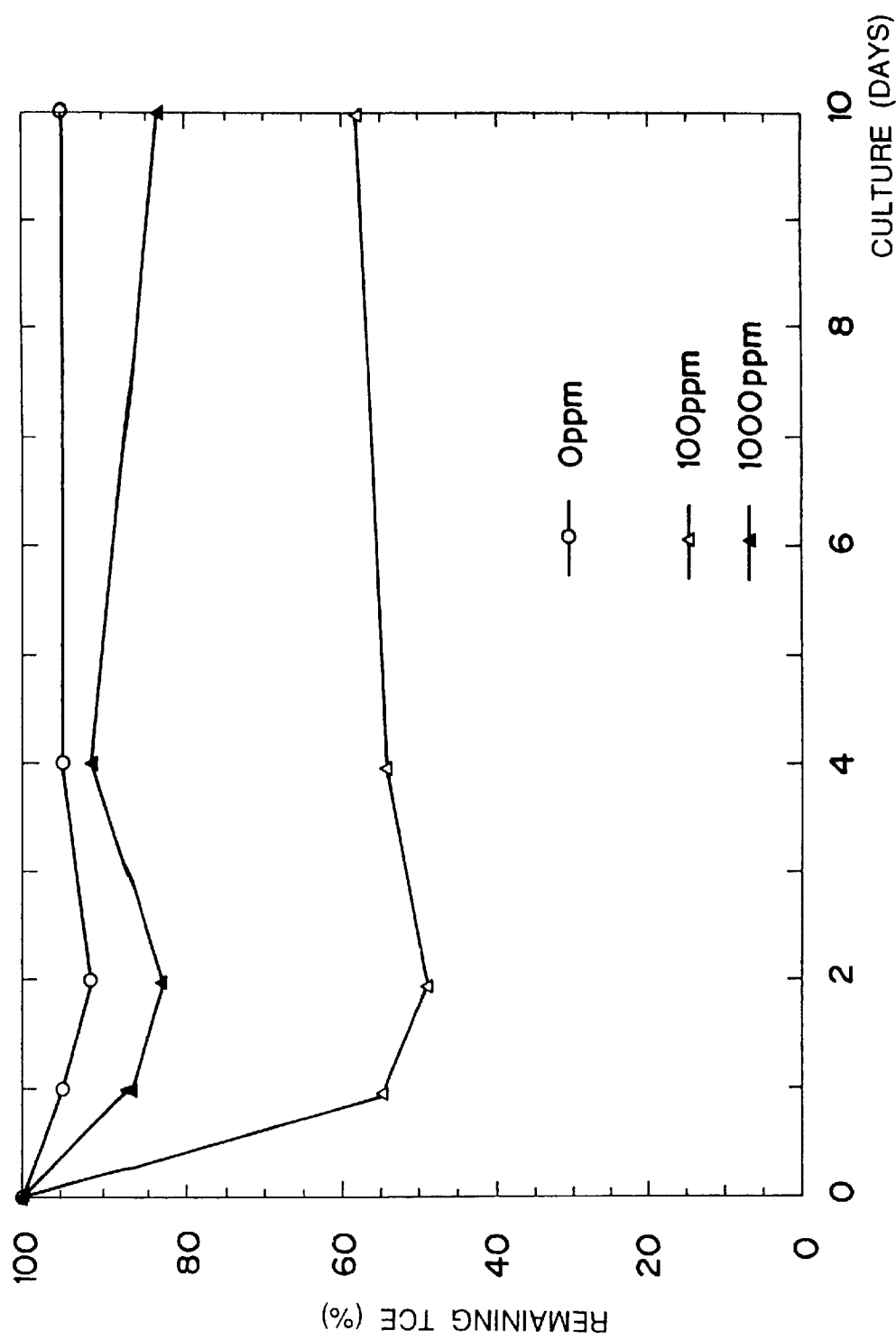
FIG. 9 shows the influence of phenol concentration on TCE degradation in Example 7.

As shown in FIG. 9, when phenol concentration was 100 ppm, a TCE degradation of about 45% was observed in one day. On the contrary, in the case of a phenol concentration of 1,000 ppm and in the case of no phenol, the degradation of TCE scarcely proceeded.

Figure 10:
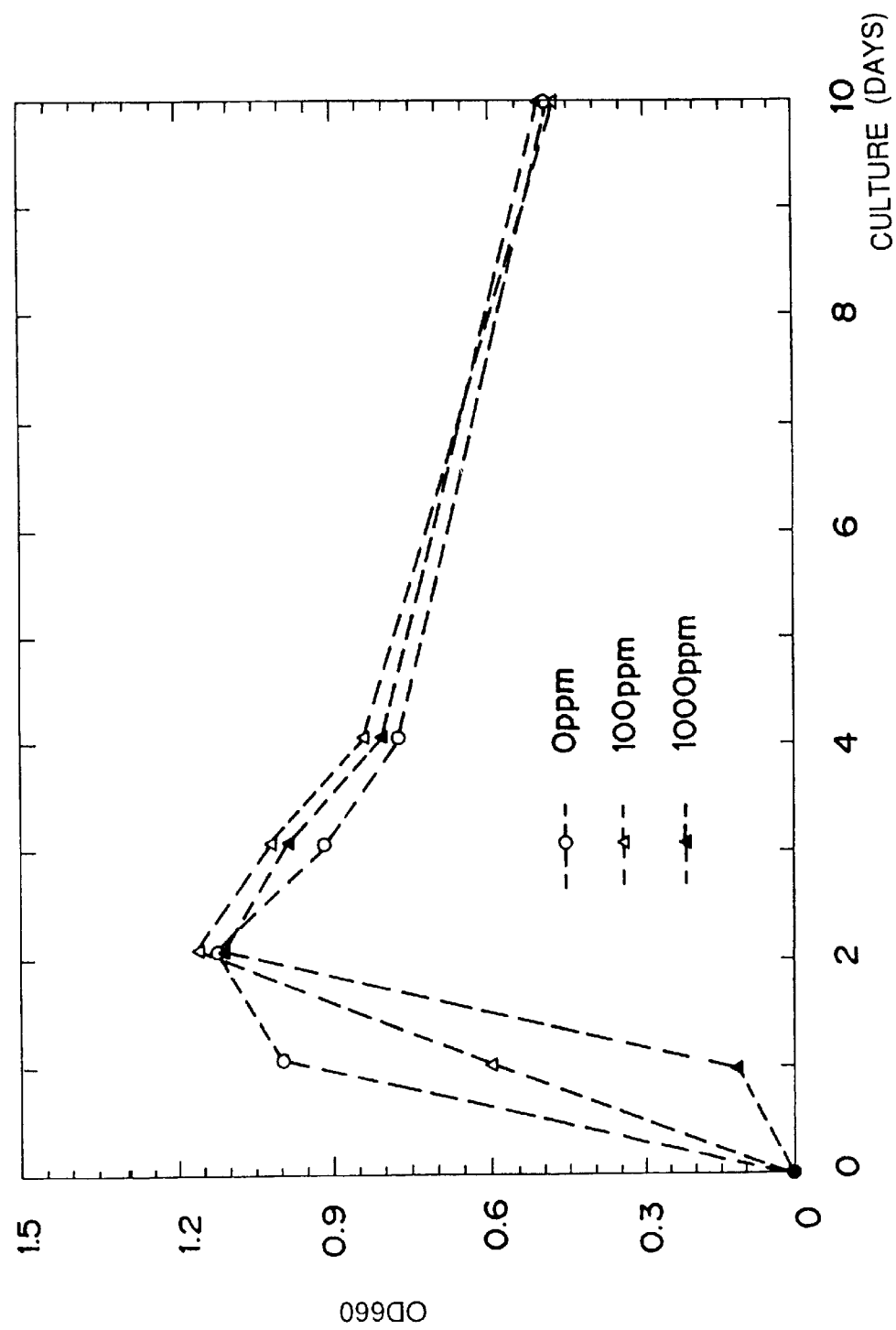
FIG. 10 shows the influence of phenol concentration on the growth of an strain KK01 in Example 7.

On the other hand, as shown in FIG. 10, bacteria growth proceeded similarly at phenol concentrations of 0 and 100 ppm. In addition, when the phenol concentration was 1,000 ppm, a maximum bacteria number and days taken to reach the maximum bacteria number were equal to cases where the phenol concentrations were 0 and 100 ppm. However, the initial bacteria growth curve in the case of the 1,000 ppm concentration did not show a convex form, which meant the hindrance of the bacteria growth.

As described above, when the phenol concentration was 1,000 ppm, the maximum bacteria number and the days taken to reach the maximum bacteria number were equal to the case where the phenol concentration was 100 ppm, but nevertheless, the degradation of TCE scarcely proceeded. This fact indicates that the bacteria numbers similarly increase at concentrations of 100 ppm and 1,000 ppm, but the activation of the bacteria degradation ability took place only in the case of 100 ppm representing the convex bacteria growth curve.

EXAMPLE 8

In general, it is considered that aromatic compound-assimilating bacteria such as a Pseudomonas genus are present in a soil. Now, 1 g of a brown forest earth sampled in Kanagawa Prefecture of Japan was added to 15 ml of an M9 culture medium in which the concentration of phenol was adjusted to 200 ppm, and shake culture was then carried out at 30° C. for 3 days. Afterward, 100 $\mu$l of the thus shake-cultured medium was transferred to a similar culture medium, and then further shake-cultured at 30° C. for 3 days. This medium was plate-counted on an agar plate culture medium having a similar composition (containing 200 ppm of phenol), and as a result, bacteria of $10^6$ to $10^7$ cells/g wet soil were counted.

One gram of the soil including the confirmed aromatic compound-assimilating bacteria was added to 15 ml of an M9 culture medium in which phenol concentration and TCE initial concentration was adjusted to 200 ppm and 15 ppm, respectively, followed by shake culture at 30° C. at 120 rpm for 7 days. Afterward, a TCE degradation ratio was determined in the same manner as described above, and as a result, a TCE degradation of about 50% was observed. That is, it was confirmed that the bacteria capable of degrading TCE in the presence of phenol were present in the soil.

On the basis of the above-mentioned results, experiments were carried out to inspect the phenol concentration which had an influence on the TCE degradation of native aromatic compound-assimilating and TCE-degrading bacteria. That is, the TCE degradation per gram of the soil was measured in the same manner as in Example 5. The obtained results are shown in FIGS. 11 and 12.

Figure 11:
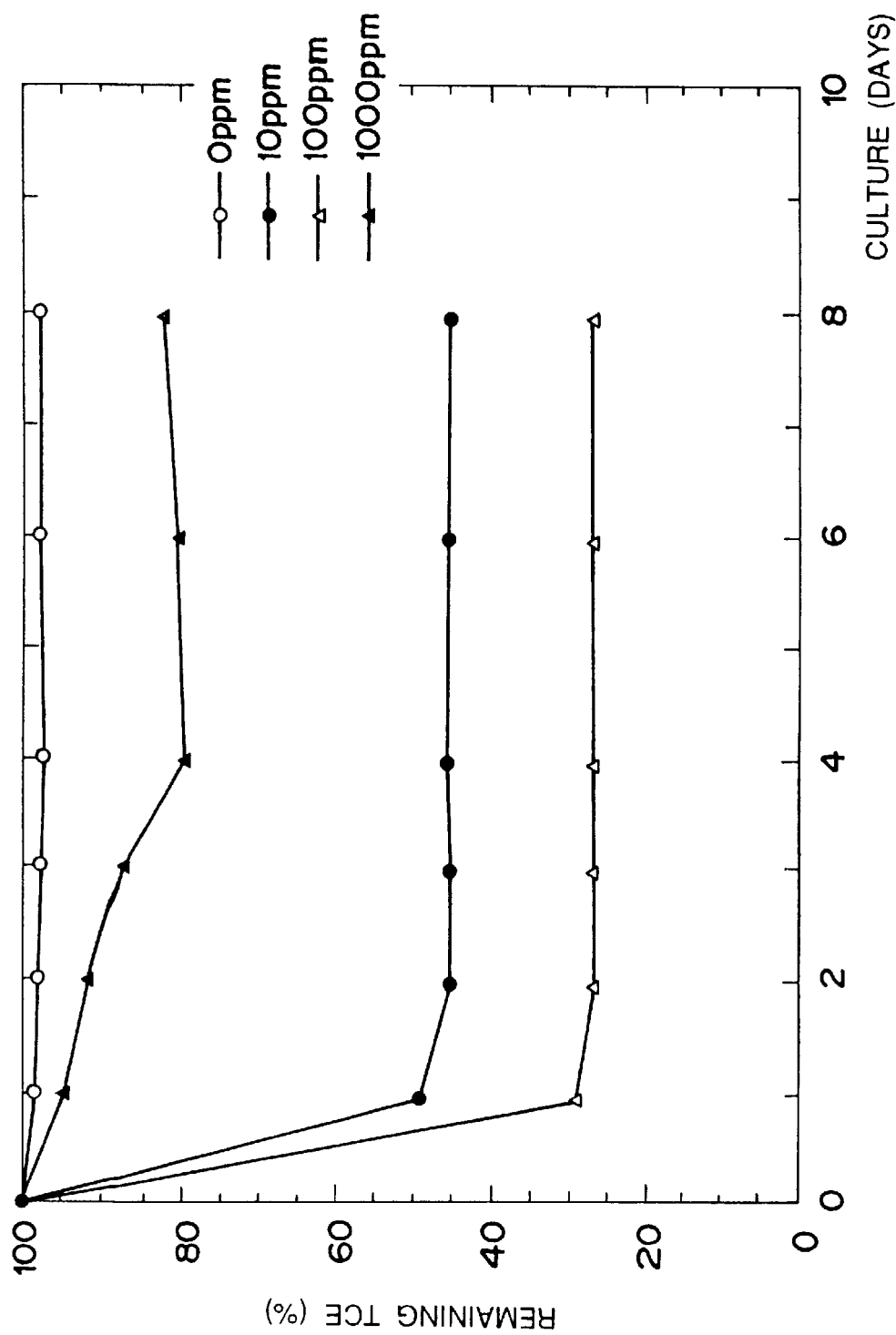
FIG. 11 shows the influence of phenol concentration on TCE degradation in Example 8.

According to the results of FIG. 11, when the phenol concentration was 100 ppm, the maximum degradation was observed, and a TCE degradation of about 70% in one day was observed. Next, when the phenol concentration was 10 ppm, a TCE degradation of about 50% in one day was observed. In addition, when the phenol concentration was 1,000 ppm, the extremely slow degradation was observed.

Figure 12:
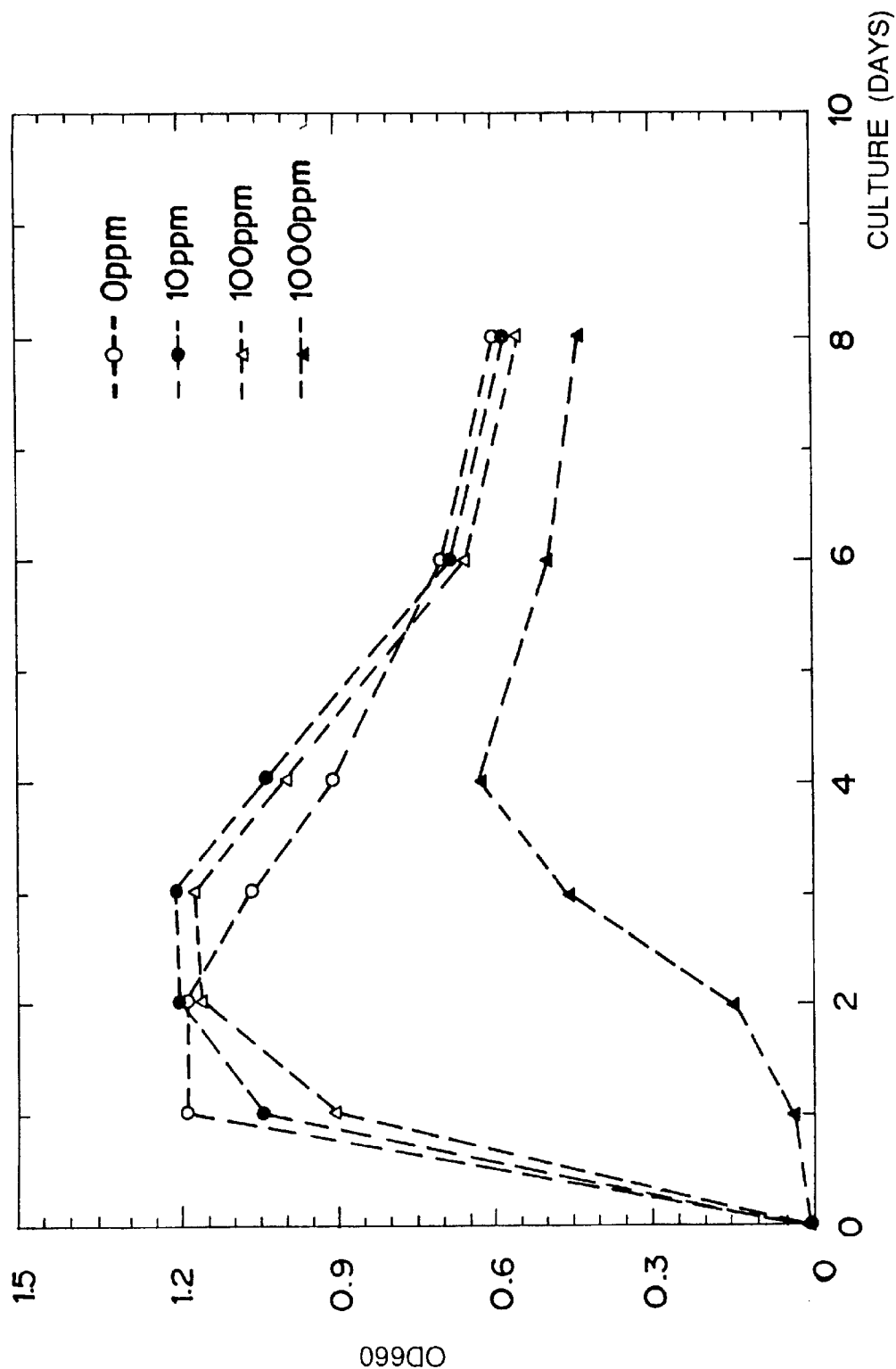
FIG. 12 shows the influence of phenol concentration on the growth of native (indigenous) bacteria in Example 8.
Figure 13:
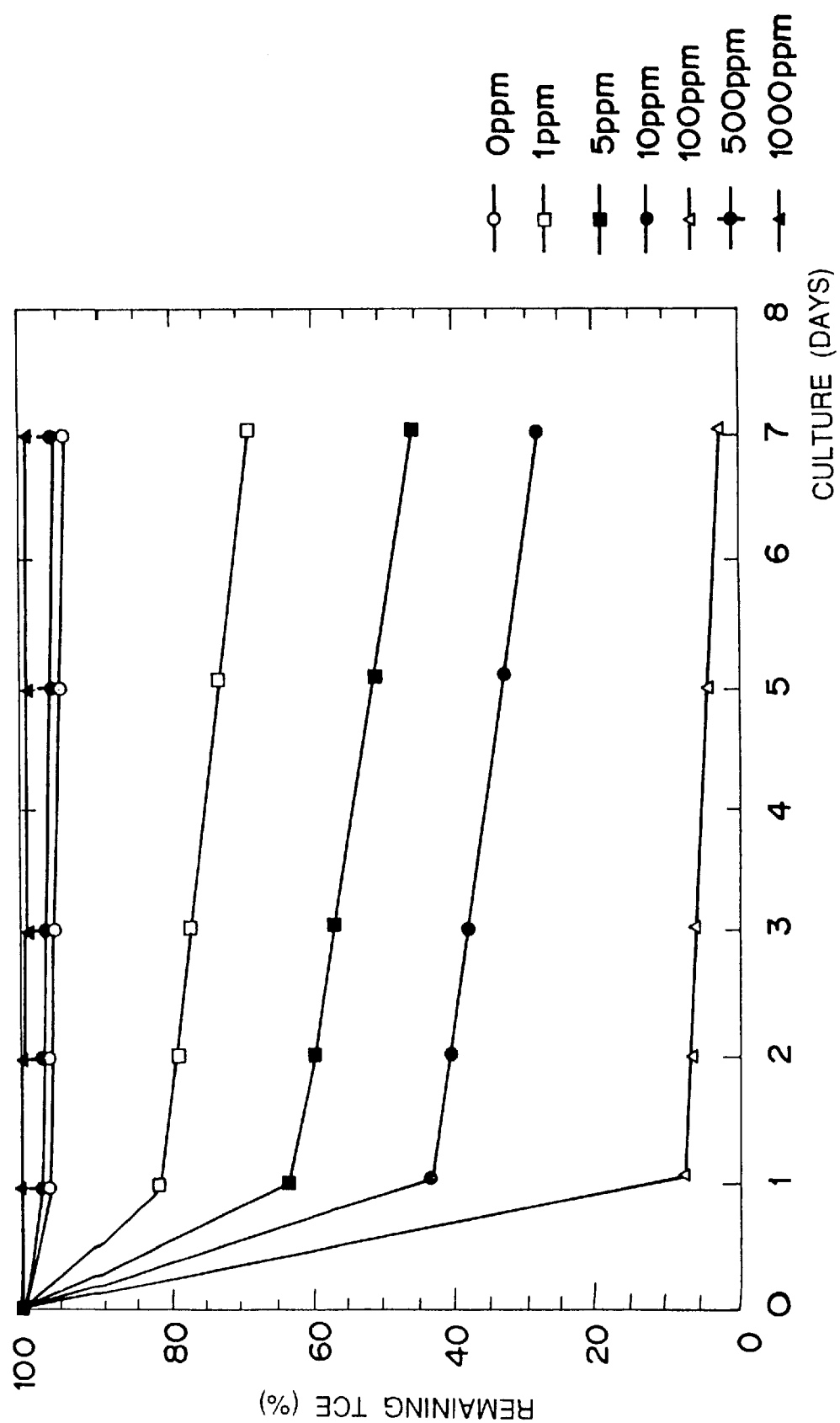
FIG. 13 shows the influence of phenol concentration on TCE degradation in Example 9.

On the other hand, as shown in FIG. 12, with regard to the growth of the bacteria, when the phenol concentrations were 0, 10 and 100 ppm, all of their initial growth curves showed a convex conformation, as in the case of a strain KK01. However, when the phenol concentration was 1,000 ppm, the bacteria growth was definitely hindered.

EXAMPLE 9

15 ml of a culture medium [an M9 culture medium containing 0.2% sodium glutamate and phenol having each of predetermined concentrations {0, 1, 5, 10, 100, 500 and 1,000 ppm (mg/kg of a wet soil)}] and a strain KK01 (0.1 ml of a KK01 species culture medium) were added to a serum bottle containing 100 g of a sterilized loamy layer of the Kanto District polluted with TCE at 5 ppm (5 mg of TEC per kg of the wet soil) and having a moisture content of 90%, and they were then uniformly mixed. Next, the serum bottle was crimp-sealed with a butyl rubber septum and an aluminum seal, followed by stationary culture at 30° C. Afterward, 0.1 ml of the gaseous phase in the serum bottle was sampled with time, and ratios of remaining TCE were determined, as in the case of Example 5. The obtained results are shown in FIG. 3.

It can be understood that a degrading ability substantially corresponding to the case of the 5 ppm TCE culture medium system of Example 6 can be obtained also in the soil system, depending upon the concentration of phenol.

Therefore, in view of the results in Example 6 and FIGS. 7 and 8, i.e., on the basis of the data of a bacteria growth curve obtained by the experiment of a culture medium batch system, there can be set a practically effective concentration of an inducer in the case of the soil.

EXAMPLE 10

The same procedure as in Example 5 was carried out except that cis-1,2-dichloroethylene (cis-DCE) was used as a material to be degraded and the concentration of this cis-DCE was set to 13 ppm. The obtained results are shown in FIGS. 14 and 15.

Figure 14:
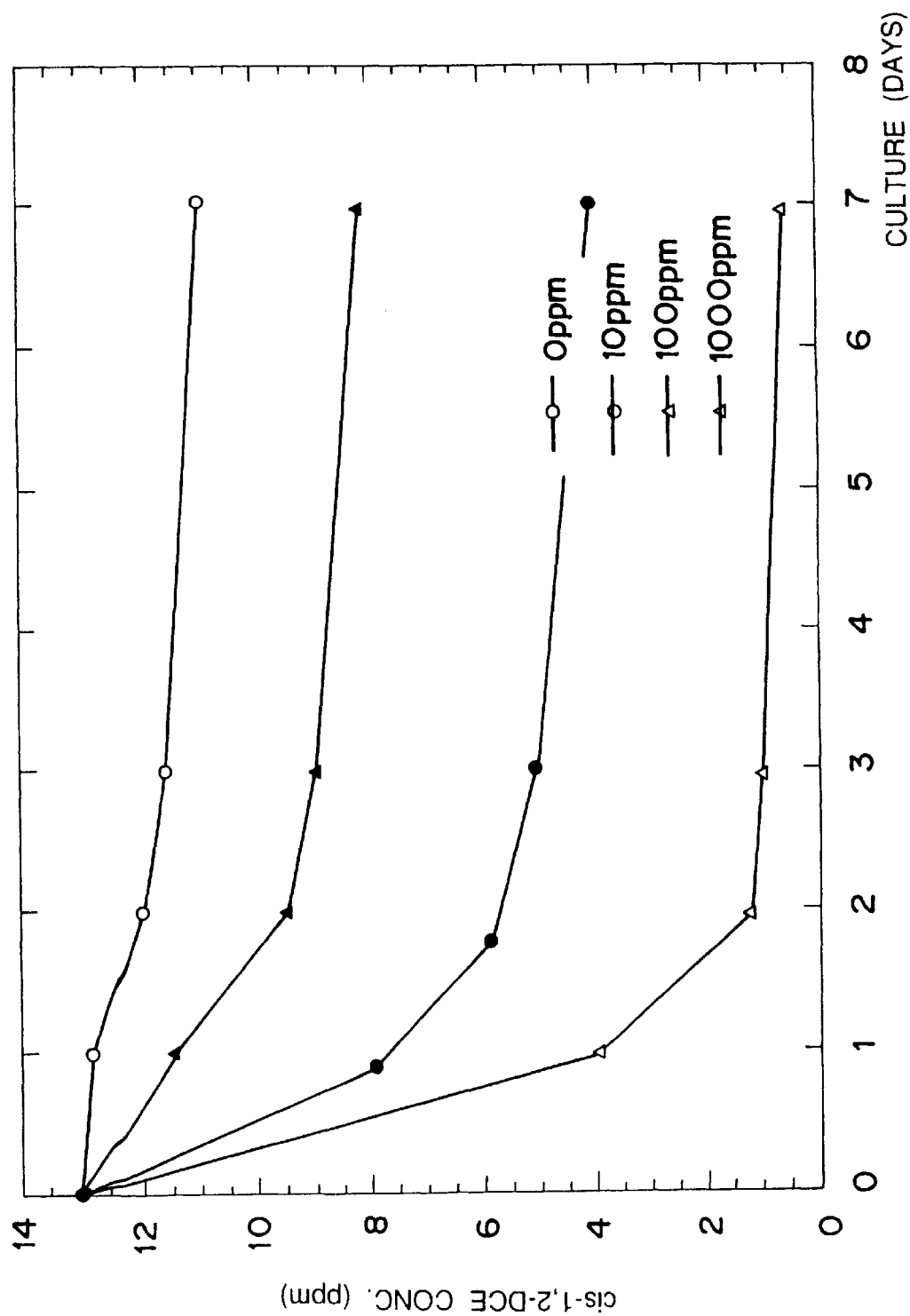
FIG. 14 shows the influence of phenol concentration on cis-DCE degradation in Example 10.

As shown in FIG. 14, when the phenol concentration was 100 ppm, cis-DCE was degraded from 13 ppm to 1 ppm or less in 7 days. On the contrary, when the phenol concentration was 10 ppm, cis-DCE was degraded only to 4 ppm in 7 days. In addition, when the phenol concentration was 1,000 ppm, cis-DCE was degraded only to 8 ppm in the same days.

Figure 15:
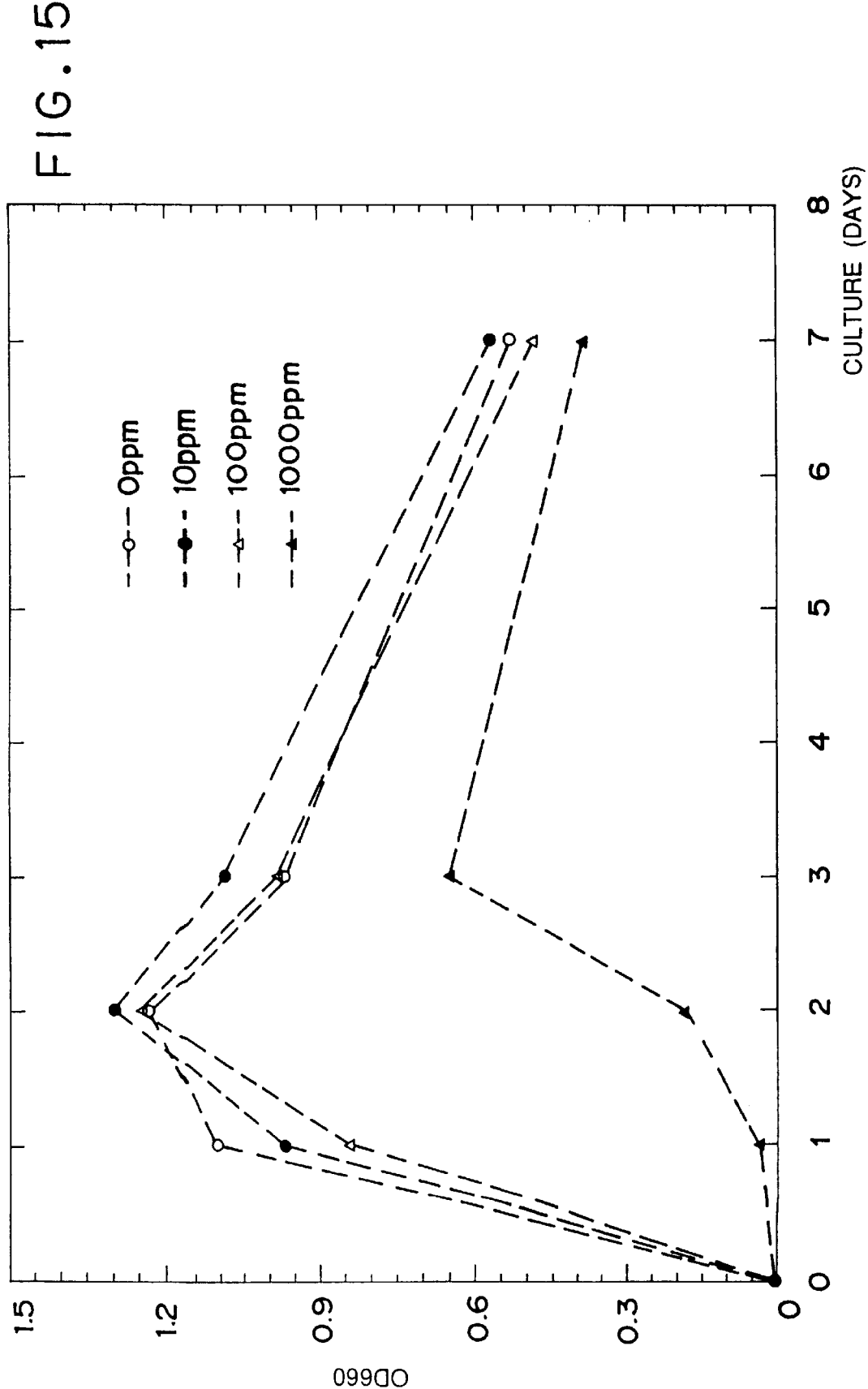
FIG. 15 shows the influence of phenol concentration on the growth of a strain KK01 in Example 10.

On the other hand, as shown in FIG. 15, with regard to initial bacteria growth characteristics, when the phenol concentrations were 0, 10 and 100 ppm, all of their initial growth curves showed a convex form. A maximum bacteria number O.D.=1.2–1.3 was obtained, and culture days taken to reach the maximum were two days, which was common in the cases of these phenol concentrations.

When the phenol concentration was 1,000 ppm, the growth of the bacteria were apparently hindered, and the maximum bacteria number O.D. was about 0.7 after 3 days.

EXAMPLE 11

The same cultivation as in Example 5 was carried out except that phenol was replaced with p-cresol as a TCE degrading inducer. In this case, the concentration of TCE was set to 15 ppm, and the concentrations of p-cresol were changed to 0 ppm, 10 ppm, 100 ppm and 1,000 ppm so as to inspect the influence of the p-cresol concentrations. The obtained results are shown in FIGS. 16 and 17.

Figure 16:
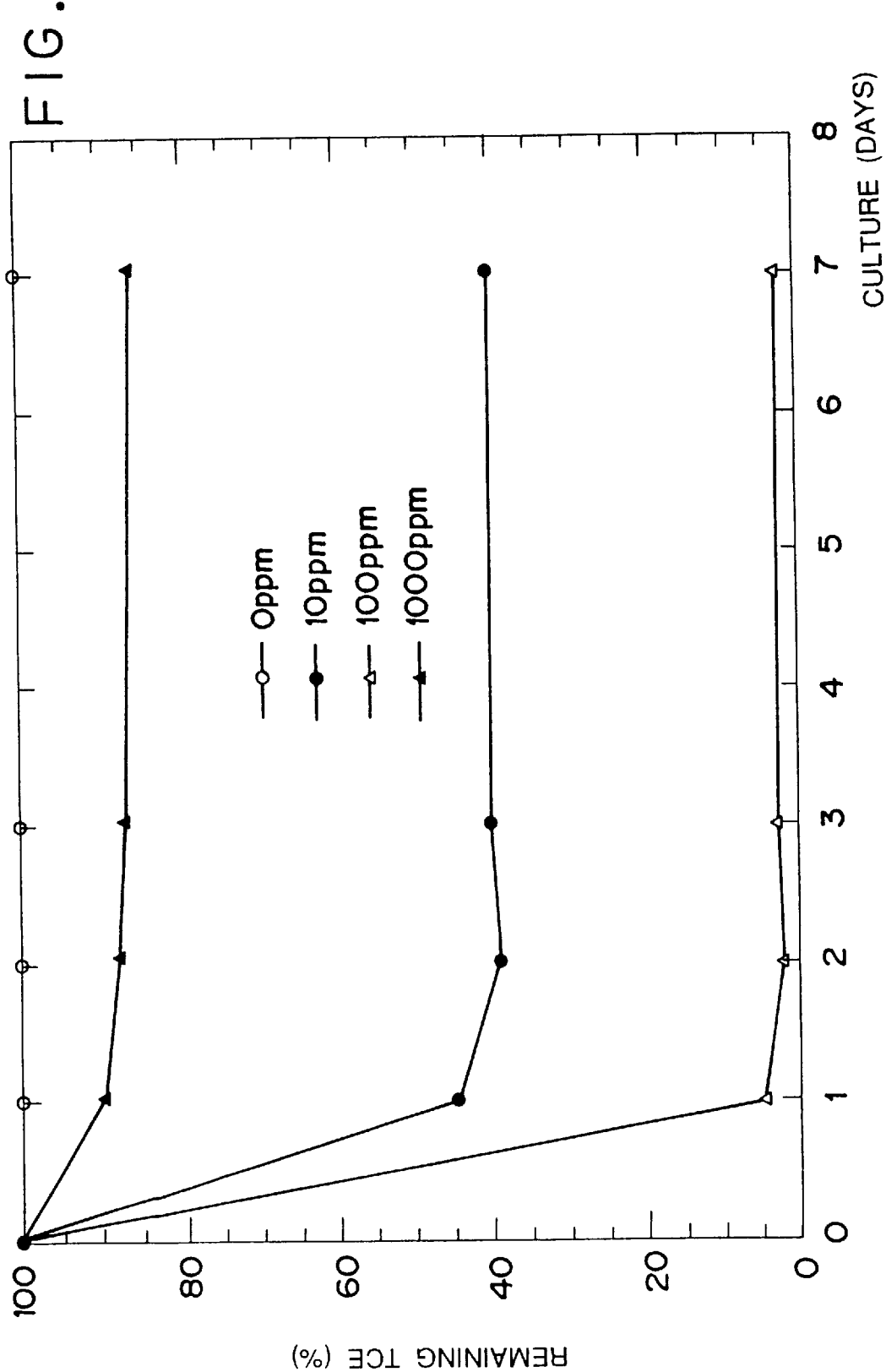
FIG. 16 shows the influence of p-cresol concentration on TCE degradation in Example 11.

As shown in FIG. 16, when the p-cresol concentrations were 100 ppm and 10 ppm, the degradations of TCE were 98% or more and at most 62% or so in two days, respectively. On the contrary, when the p-cresol concentration was 1,000 ppm, the TCE degradation was limited to about 14%.

Figure 17:
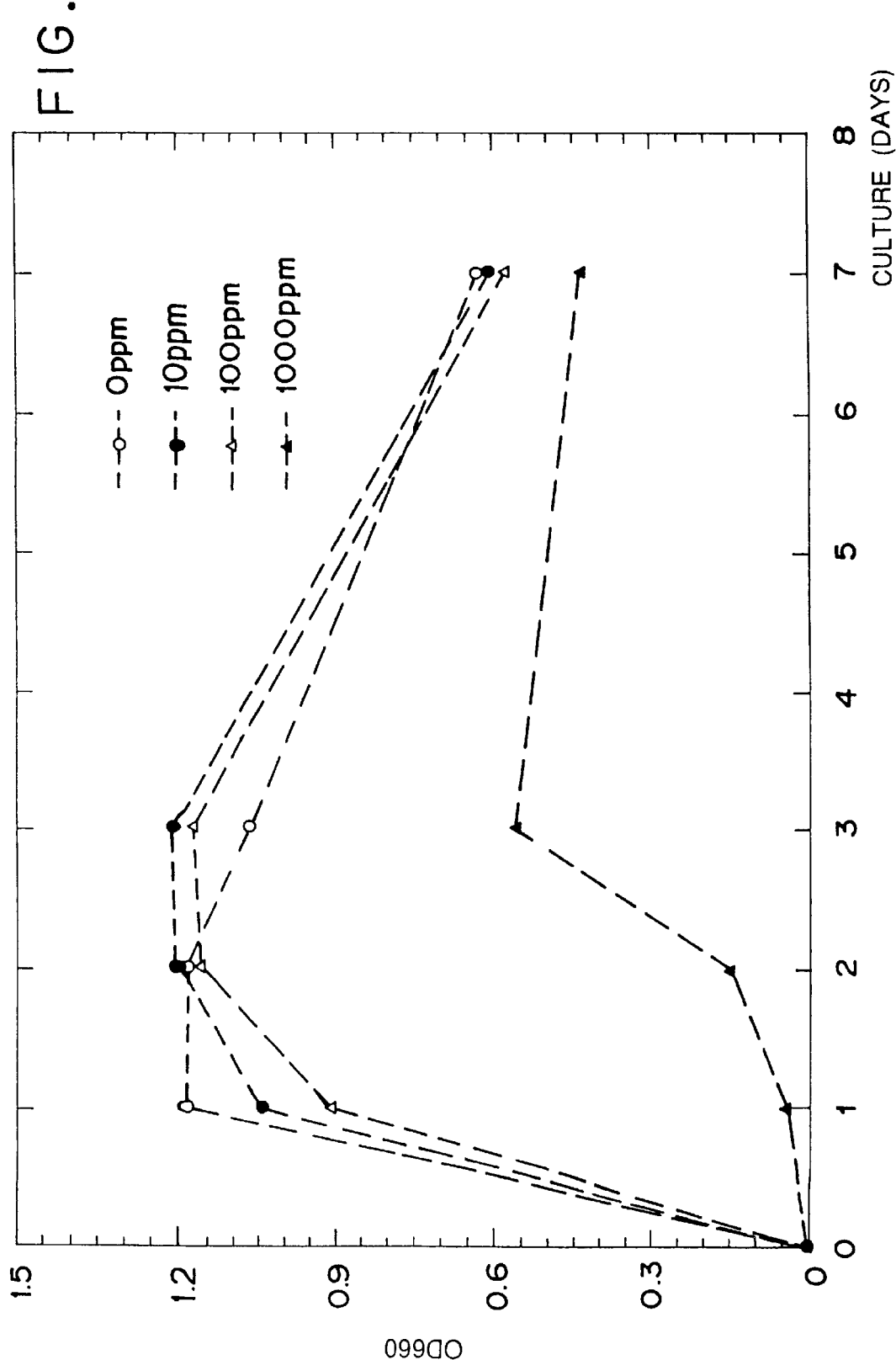
FIG. 17 shows the influence of p-cresol concentration on the growth of a strain KK01 in Example 17.

On the other hand, as shown in FIG. 17, in all the cases of p-cresol concentrations of 0, 10 and 100 ppm, initial bacteria growth characteristics could be represented by curves of a convex form. When the p-cresol concentration was 1,000 ppm, the bacteria growth was clearly hindered.

EXAMPLE 12

Figure 18:
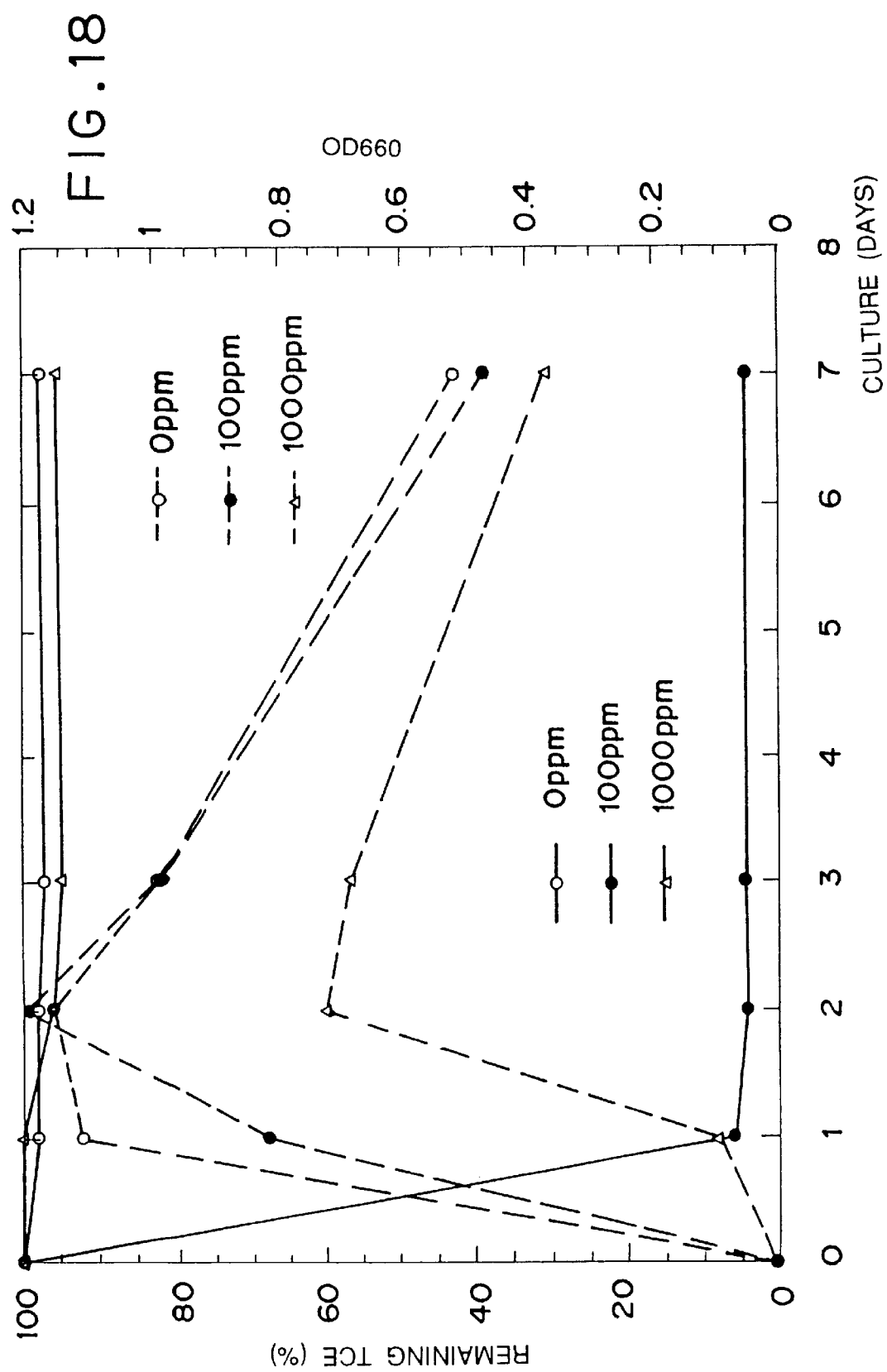
FIG. 18 shows the influence of phenol concentration on the growth of a strain BH and TCE degradation in Example 12.

An experiment was carried out by the same procedure as in Example 5 except that a *Pseudomonus putida* strain BH was used as TCE degrading bacteria. In this case, an M9 culture medium was used in which pH and TCE concentration were adjusted to 7.6 and 5 ppm, respectively. The results are shown in FIG. 18.

When a phenol concentration was 100 ppm, an initial bacteria growth curve showed a convex form, and at this time, TCE degradation proceeded about 95% in one day.

On the contrary, when the phenol concentration was 1,000 ppm, the bacteria growth was clearly hindered, and TCE was scarcely degraded.

The present invention has the following effects.

According to the present invention, a method for obtaining microorganisms having a TCE degrading ability from intestines of termites can be established, and this method permits obtaining the microorganisms suitable for the biodegradation treatment of TCE contained in waste water or the like.

Furthermore, by using the microorganisms obtained by the above-mentioned method, waste water or the like containing TCE can be effectively biodegraded.

The present invention can provide a sufficiently practical method for remediating a soil by the utilization of the degradation of TCE compounds with the microorganisms in the soil.

Additionally, according to the present invention, the concentration of an inducer for heightening a degrading activity per unit of the microorganisms for degrading chlorinated organic compounds can be estimated from initial growth characteristics of the bacteria, and so an effective biodegradation reaction showing the high degrading activity can be provided even under a small bacteria number.

What is claimed is:

1. A method for biodegrading trichloroethylene which comprises the step of:

bringing an aqueous medium containing trichloroethylene into contact with *Pseudomonas cepacia* strain KK 01 (FERM BP-4235).

2. A biodegradation method for degrading a chlorinated organic compound by bringing *Pseudomonas cepacia* strain KK 01 (FERM BP-4235), whose degrading activity can be induced with the aid of an inducer, into contact with said chlorinated organic compound in the presence of said inducer to degrade said chlorinated organic compound, the amount of said inducer being such as to meet the following relation $$2\int_0^T f(t)dt - T \cdot f(T) \geq 0$$

wherein T is a culture time when a bacterial number y is maximum, when said *Pseudomonas cepacia* strain KK 01 (FERM BP-4235) is cultured by a batch system in the presence of said inducer and the growth curve of said *Pseudomonas cepacia* strain KK 01 (FERM BP-4235) is close to y=f (t), wherein said y is a bacteria number determined by an optical density (O.D.), and t is a culture time.

3. The biodegradation method according to claim 2 wherein said chlorinated organic compound is a chlorinated ethylene.

4. The biodegradation method according to claim 3 wherein said chlorinated ethylenes are trichloroethylene or dichloroethylene (DCE).

5. The biodegradation method according to claim 2 wherein said inducer is an aromatic compound.

6. The biodegradation method according to claim 5 wherein said aromatic compound comprises at least one of phenol, toluene, o-cresol, m-cresol and p-cresol.

7. The biodegradation method according to claim 2 wherein the amount of said inducer is 50% or more of that of said chlorinated organic compound.

* * * * *

UNITED STATES PATENT AND TRADEMARK OFFICE
CERTIFICATE OF CORRECTION

PATENT NO. : 5,993,658
DATED : November 30, 1999
INVENTOR(S) : KINYA KATO ET AL.

Page 1 of 4

It is certified that error appears in the above-identified patent and that said Letters Patent is hereby corrected as shown below:

ON THE TITLE PAGE

[57] Abstract:

Line 8, "an" should read --a--.

COLUMN 1:

Line 23, "an" should read --a--; and
      Line 49, "an" should read --a--.

COLUMN 3:

Line 66, "bacteria" should read --number of bacteria--; and
      Line 67, "number" should be deleted.

COLUMN 4:

Line 21, "an" should read --a--; and
      Line 62, "an" should read --a--.

COLUMN 5:

Line 18, "concept." should read --concepts.--;
      Line 26, "chlorinated *Nasutitermes*" should read --chlorinated organic compounds.
           In the first place, the first concept of the present invention will be described in detail.

UNITED STATES PATENT AND TRADEMARK OFFICE
CERTIFICATE OF CORRECTION

PATENT NO. : 5,993,658

DATED : November 30, 1999

INVENTOR(S) : KINYA KATO ET AL.

It is certified that error appears in the above-identified patent and that said Letters Patent is hereby corrected as shown below:

A method for biodegrading TCE of the present invention is characterized by comprising the step of bringing an aqueous medium containing trichloroethylene into contact with microorganisms derived from intestines of termites which have an ability to degrade trichloroethylene, thereby degrading trichloroethylene.

Furthermore, a method for remediating a soil is characterized by comprising the step of bringing, in the soil, trichloroethylene into contact with microorganisms derived from intestines of termites which have an ability to degrade trichloroethylene, thereby degrading trichloroethylene to remediate the soil.

The microorganisms derived from the intestines of termites which can be used in the method of the present invention can be obtained by, for example, sterilizably washing the surfaces of the termites, taking intestines out of the termites and crushing them in a suitable solution, and isolating a strain from a part of the mixture containing the crushed intestines, this strain being screened on the basis of the TCE degrading ability. In the present invention, the various kinds of termites can be used, but preferable examples of the termites include Nasutitermes takasagoensis, *Nasutitermes*--;

UNITED STATES PATENT AND TRADEMARK OFFICE
CERTIFICATE OF CORRECTION

PATENT NO.    : 5,993,658
DATED         : November 30, 1999
INVENTOR(S)   : KINYA KATO ET AL.                    Page 3 of 4

It is certified that error appears in the above-identified patent and that said Letters Patent is hereby corrected as shown below:

COLUMN 5

Line 50, "organic compounds." should be deleted; and
　　Line 51-67, Lines 51 to 67 should be deleted.

COLUMN 6:

Lines 1-8, Lines 1 to 8 should be deleted; and
　　Line 9, "*takasagoensis*," should be deleted.

COLUMN 7:

Line 54, "supposed" should read --supported--.

COLUMN 8:

Line 12, "workers" should read --worker--.

COLUMN 10:

Line 14, "workers" should read --worker--; and
　　Line 50, "crimp-seald" should read --crimp-sealed--.

COLUMN 12:

Line 55, "were more" should read --was--.

COLUMN 14:

Line 5, "TEC" should read --TCE--.

UNITED STATES PATENT AND TRADEMARK OFFICE
CERTIFICATE OF CORRECTION

PATENT NO.    : 5,993,658
DATED         : November 30, 1999
INVENTOR(S)   : KINYA KATO ET AL.

It is certified that error appears in the above-identified patent and that said Letters Patent is hereby corrected as shown below:

COLUMN 15:

Line 3, "Pseudomonus" should read --Pseudomonas--.

Signed and Sealed this

Ninth Day of January, 2001

Attest:

Attesting Officer

Q. TODD DICKINSON
Commissioner of Patents and Trademarks